(12) United States Patent
Chiu et al.

(10) Patent No.: US 7,993,821 B2
(45) Date of Patent: Aug. 9, 2011

(54) METHODS AND APPARATUS FOR THE ISOLATION AND ENRICHMENT OF CIRCULATING TUMOR CELLS

(75) Inventors: Daniel T. Chiu, Seattle, WA (US); Jason S. Kuo, Seattle, WA (US)

(73) Assignee: University of Washington, Seattle, WA (US)

(*) Notice: Subject to any disclaimer, the term of this patent is extended or adjusted under 35 U.S.C. 154(b) by 35 days.

(21) Appl. No.: 11/766,044

(22) Filed: Jun. 20, 2007

(65) Prior Publication Data

US 2008/0248499 A1    Oct. 9, 2008

Related U.S. Application Data

(63) Continuation-in-part of application No. 11/202,416, filed on Aug. 11, 2005.

(51) Int. Cl.
*C12Q 1/00* (2006.01)
(52) U.S. Cl. ............................................ 435/4; 435/7.23
(58) Field of Classification Search .................. None
See application file for complete search history.

(56) References Cited

U.S. PATENT DOCUMENTS

| | | | |
|---|---|---|---|
| 4,923,608 A | 5/1990 | Flottmann et al. | |
| 5,234,594 A | 8/1993 | Tonucci et al. | |
| 5,726,026 A * | 3/1998 | Wilding et al. | 435/7.21 |
| 5,731,211 A * | 3/1998 | Ohlin | 436/179 |
| 5,837,115 A | 11/1998 | Austin et al. | |
| 6,623,860 B2 | 9/2003 | Hu et al. | |
| 6,720,157 B2 | 4/2004 | Indermuhle et al. | |
| 6,730,516 B2 | 5/2004 | Jedrejewski et al. | |
| 6,949,355 B2 * | 9/2005 | Yamanishi et al. | 435/34 |
| 7,217,542 B2 | 5/2007 | Tyvoll et al. | |
| 2002/0164825 A1 * | 11/2002 | Chen | 436/526 |
| 2005/0003411 A1 | 1/2005 | Chiu et al. | |
| 2007/0037172 A1 | 2/2007 | Chiu et al. | |
| 2007/0160503 A1 | 7/2007 | Sethu et al. | |
| 2007/0160504 A1 * | 7/2007 | Parthasarathy et al. | 422/102 |

FOREIGN PATENT DOCUMENTS

| | | |
|---|---|---|
| WO | WO 98/13131 A1 | 4/1998 |
| WO | WO9813131 * | 4/1998 |
| WO | WO 2006/079007 A2 | 7/2006 |
| WO | WO2006079007 * | 7/2006 |
| WO | WO 2006/104474 A2 | 10/2006 |
| WO | WO 2006/116327 A1 | 11/2006 |
| WO | WO 2006/127256 A2 | 11/2006 |
| WO | WO 2007/021409 A1 | 2/2007 |

OTHER PUBLICATIONS

"International Search Report and Written Opinion for Application No. PCT/US2006/027099, Mailed Oct. 31, 2006", 11 pages.
Kuo, Jason S. et al. "Deformability considerations in filtration of biological cells," Lab Chip, 2010, vol. 10, pp. 837-842.
Lim, D. S., et al., "Parametric investigations on the effect of channel topologies on electrophoretic separations", *Journal of Chromatography*, 1027(1-2), Elsevier Science Publishers B.V. Amsterdam, NL, Feb. 20, 2004, pp. 237-244.

* cited by examiner

*Primary Examiner* — Ann Lam
(74) *Attorney, Agent, or Firm* — Kilpatrick Townsend & Stockton LLP

(57) ABSTRACT

Embodiments in accordance with the present invention relate to methods and apparatuses for concentrating and isolating Circulating Tumor Cells (CTCs) from body fluids. One embodiment of the present invention includes a micro-fabricated or nano-fabricated device having channels configured for separating and excluding. Embodiments in accordance with the present invention utilize features that reduce the hydrodynamic pressure experienced by the cells during the separation, isolation and concentration processes, and therefore reduce the likelihood of cell lysis or other damage to the cells.

14 Claims, 29 Drawing Sheets

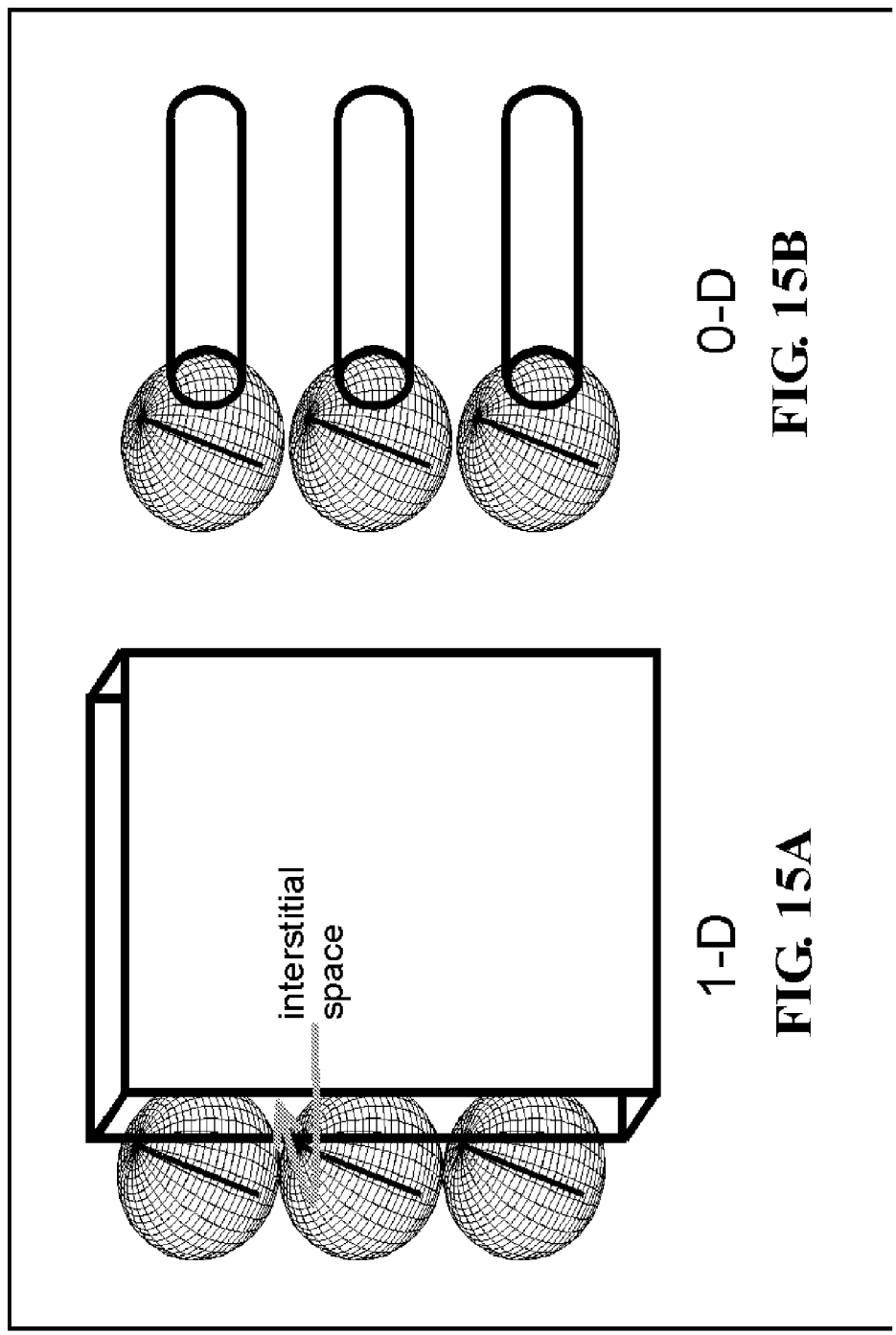
FIG. 15A 1-D
FIG. 15B 0-D

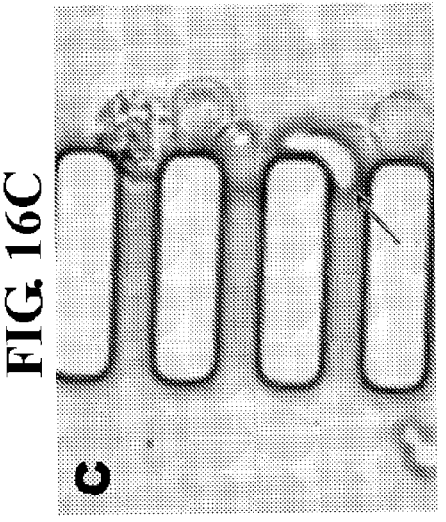
FIG. 16A  FIG. 16B  FIG. 16C
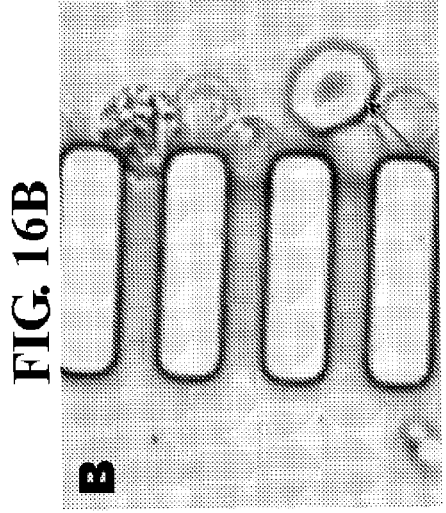
FIG. 16D  FIG. 16E  FIG. 16F
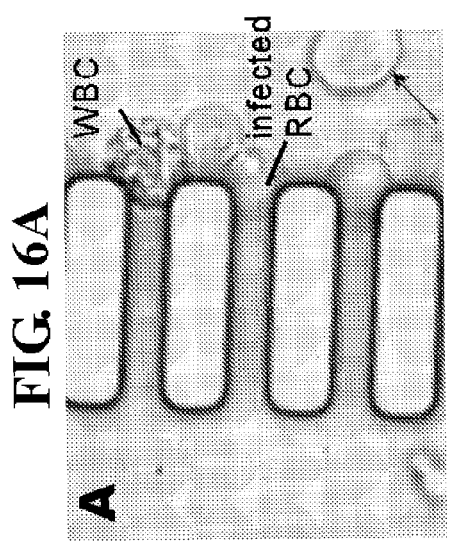
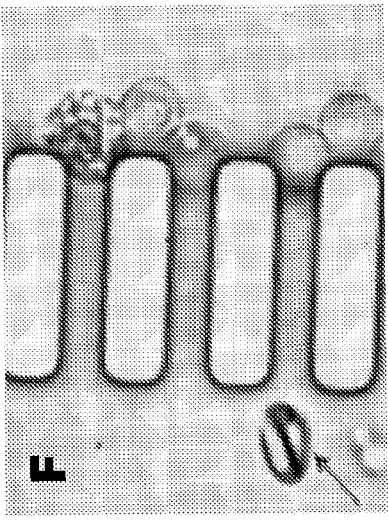
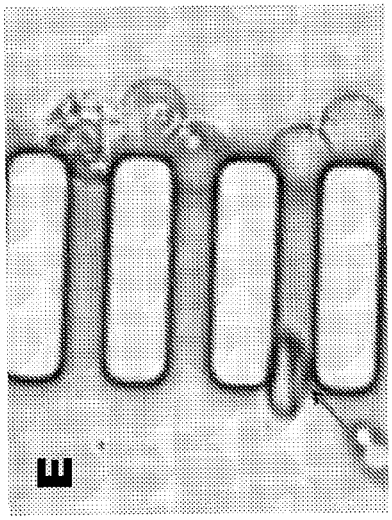
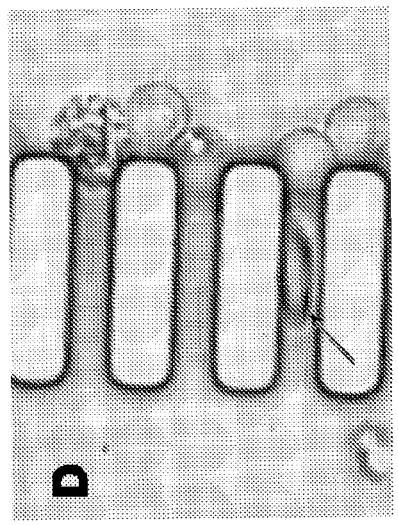

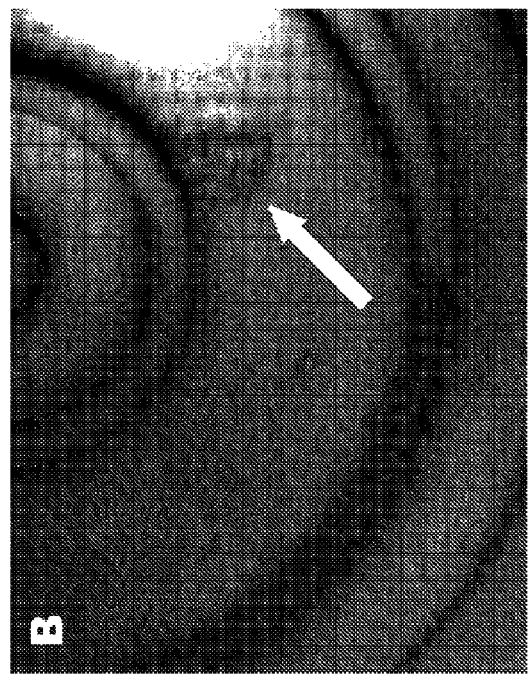
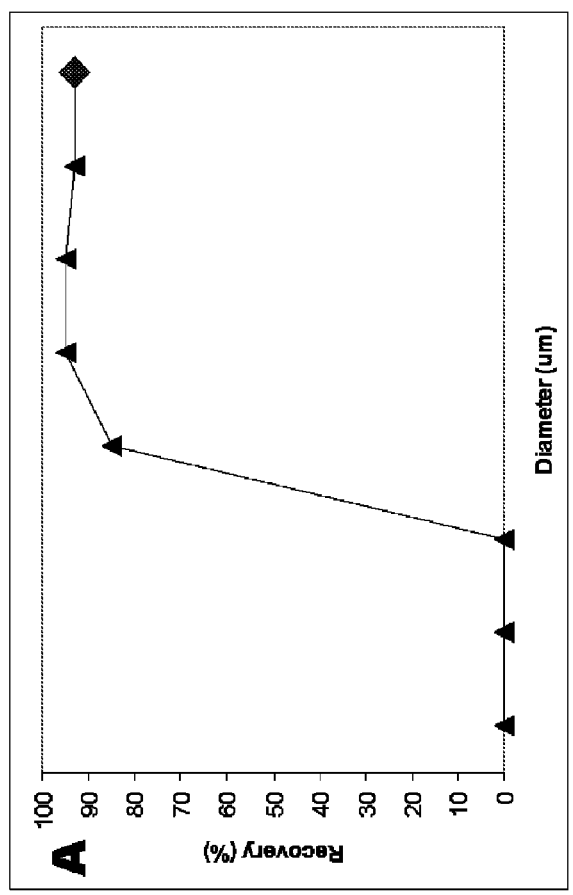
FIG. 22A.
FIG. 22B.

FIG. 29A
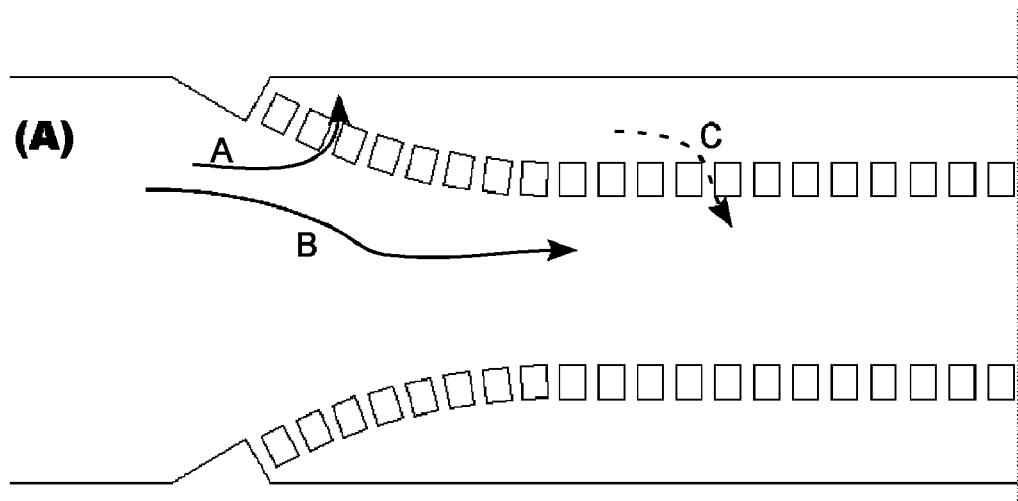
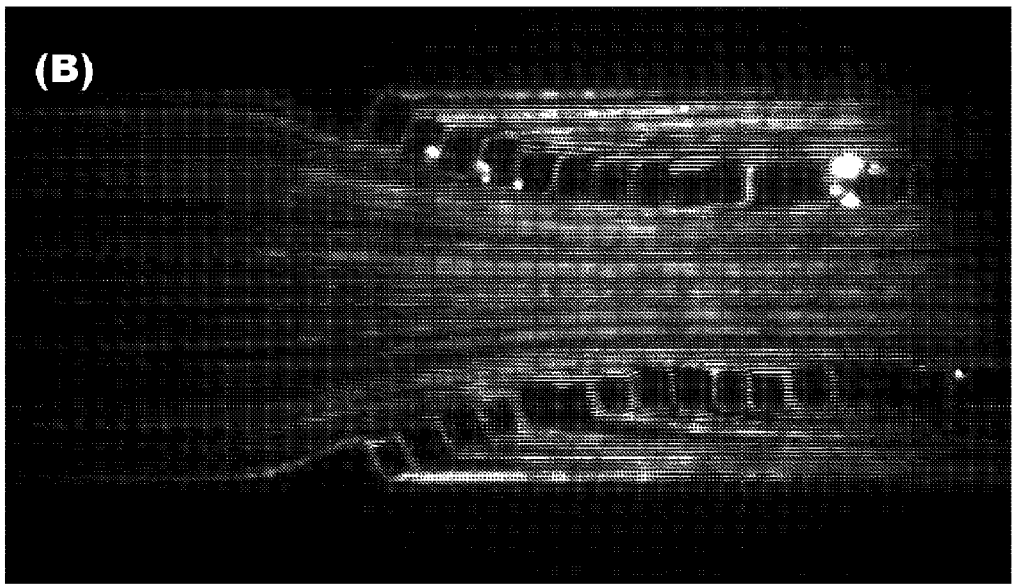
FIG. 29B

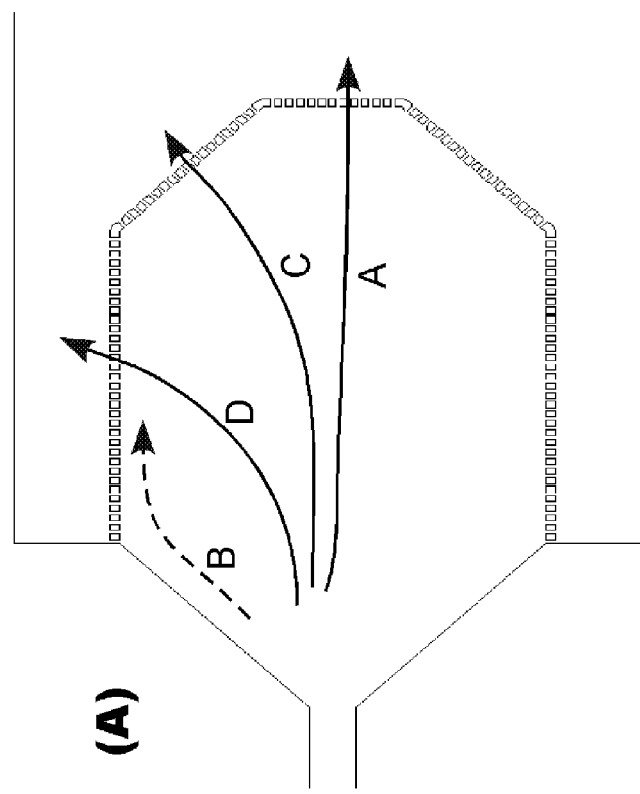
FIG. 31A
FIG. 31B

METHODS AND APPARATUS FOR THE ISOLATION AND ENRICHMENT OF CIRCULATING TUMOR CELLS

CROSS-REFERENCE TO RELATED APPLICATION

The instant nonprovisional patent application is a continuation-in-part of U.S. patent application Ser. No. 11/202,416 filed Aug. 11, 2005 and incorporated by reference in its entirety herein for all purposes.

GOVERNMENT FUNDING

The subject matter described herein was made with U.S. Government support under National Institute of Health (NIH) Grant Number R01 GM65293 and the Puget Sound Partners for Global Health Pilot Project (PSPGH). The United States Government has certain rights in the invention.

BACKGROUND OF THE INVENTION

Body fluid is a complex mixture of different cell types and biological particles. Blood, for example, includes plasma and cells (red blood cells, white blood cells, platelets) and the cells occupy about 55% of blood. Plasma is mostly water and it transfers proteins, ions, vitamins, enzymes, hormone, and other chemicals to cells in the body. Red blood cells are about 6 to 8 μm in size and serve to provide oxygen to cells. White blood cells are about 10 to 13 μm in diameter and they defend the body from disease as a part of an immune system by fighting against foreign virus and bacteria. Platelets are the smallest cells, 1.5 to 3 μm, and they stop bleeding by forming blood clots. Fluids in addition to blood, such as saliva, tear, urine, cerebral spinal fluid as well as other body fluids in contact with various organs (e.g. lung) contain mixtures of cells and bioparticles.

The type and amount of cells and bioparticles that are present in a particular body fluid (e.g. blood) includes information about the health of the organism, and in the case of an infected individual, information about the diagnosis and prognosis of the disease. For example, anemia can be diagnosed by counting the number of red blood cells within a unit volume of blood. Similarly, elevated white blood cell count is a standard screen for signs of heightened immune response, which is often due to infection.

In diseases such as HIV, the level of CD4+ T-lymphocytes (CD4+ T-cells) in blood indicates the degree of disease progression. In fact, the CDC Public Health Service recommends monitoring the level of CD4+ T-cells every 3-6 months in all HIV-infected persons as a way to initiate appropriate treatment strategies. Another example is malaria diagnosis, in which the number of parasitized erythrocytes among normal erythrocytes and leucocytes is counted. Yet another example is in cancer diagnosis and prognosis—tumor cells can exfoliate from solid tumors and transport throughout the body via the blood stream or other body fluids (e.g. lung cancer cells may exfoliate into the fluid in contact with the lung and prostate cancer cells into urine). These circulating tumor cells are present in extremely low concentrations, and their isolation and detection among the other cells present in the fluid is required for diagnosis and prognosis.

BRIEF SUMMARY OF THE INVENTION

Embodiments in accordance with the present invention relate to methods and apparatuses for concentrating and isolating Circulating Tumor Cells (CTCs) from body fluids. One embodiment of the present invention includes a micro-fabricated or nano-fabricated device having channels configured for separating and excluding. Embodiments in accordance with the present invention utilize features that reduce the hydrodynamic pressure experienced by the cells during the separation, isolation and concentration processes, and therefore reduce the likelihood of cell lysis or other damage to the cells.

BRIEF DESCRIPTION OF THE DRAWINGS

FIGS. 15A and 15B illustrate modeled views of channels with target particles.
FIGS. 16A-16F illustrate trapping of malaria-infected red blood cells (RBC) and white blood cells (WBC).

FIG. 22A illustrates the percent of breast cancer cells (MCF-7) recovered using an exemplary device (indicated with ♦).

FIG. 22B illustrates a still image of a breast cancer cell (arrow) moving through an exemplary device.

FIGS. 29A-B show an example of effusive filtration featuring constriction of the feed chute.

FIGS. 31A-B show an example of effusive filtration featuring an expansion of flow channel.

DETAILED DESCRIPTION OF THE INVENTION

Figure 1A:
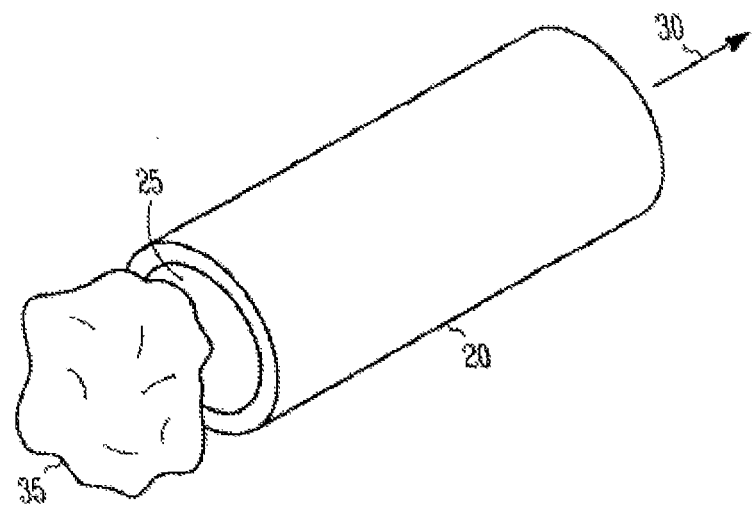
FIG. 1A illustrates a zero-dimensional channel with a target particle.

This document pertains generally to methods and systems for isolating, separating, and concentrating biological cells and biological particles from complex biofluid mixtures and, in particular but not by way of limitation, to methods and systems with features to reduce cell lysis or cellular membrane damage during cell and particle isolation and separation.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Biological cells are often sensitive to local pressure change because cellular membranes are not rigid. In filtering or isolating cells by mechanical exclusion, exposure of the cells to a high pressure environment can cause lysing. Lysis refers to the disintegration, rupturing or destruction of a cell or bacteria. With a cell, such a breakdown is caused by damage to the plasma (outer) membrane and subsequent loss of cell contents (cytoplasm, organelles or nucleus) resulting from physical insult to the cell. The present subject matter reduces the incidence of lysis in separation, concentration, filtration or isolation.

The present subject matter relates to a micro-fabricated and nano-fabricated device and method useful for separating, concentrating and isolating microscopic or nanoscopic objects such as biological cells, macromolecules, colloidal particles, particulates, or micro-beads and nano-beads using an array of one-dimensional channels. The device may be used to isolate, purify, and concentrate a subpopulation of biological cells to facilitate clinical diagnosis of diseases such as malaria, AIDS and cancer.

As used herein, a fluid can include a liquid or a gas and an object or target particle can include a cell, a bacteria, a virus, a biological nano-particulate, a biological micro-particulate or other object. The target particle can include an organic or inorganic object.

Figure 1B:
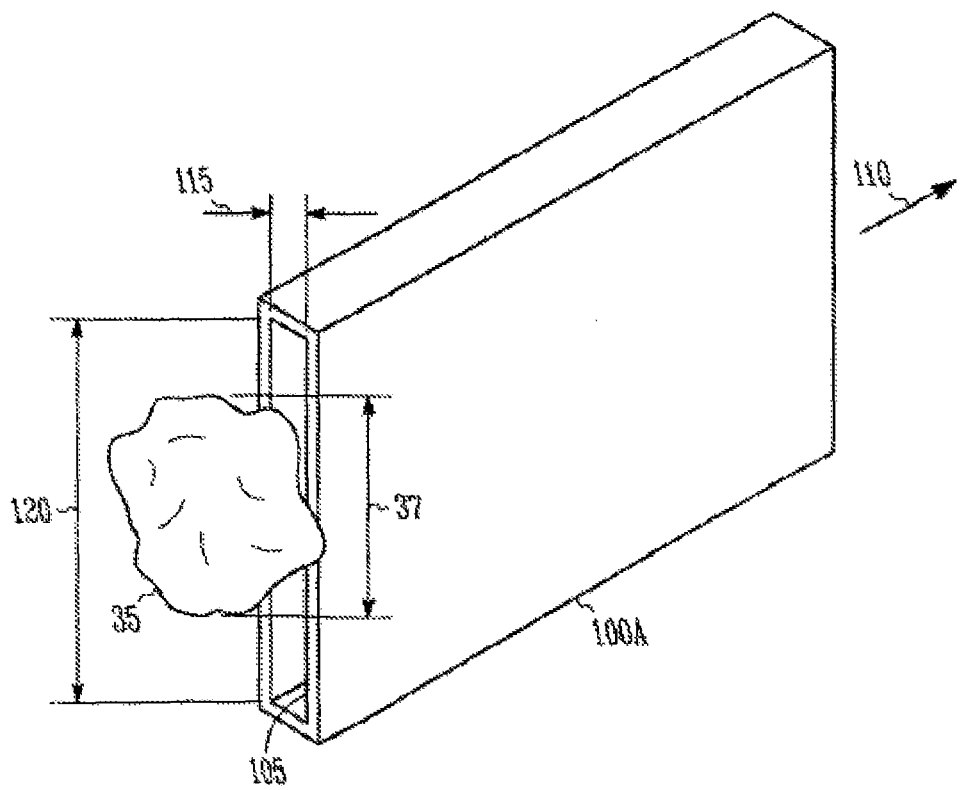
FIG. 1B illustrates a one-dimensional channel with a target particle.

FIGS. 1A and 1B illustrate sample geometry for mechanically excluding a cell, particulate or other immiscible objects from the immersed carrier fluid. FIG. 1A illustrates a geometric configuration where circular channel 20 is used to exclude target particle 35. In this figure, target particle 35 is disposed near lumen 25 of channel 20 and arrow 30 denotes the fluid flow direction, which is a manifestation of a pressure differential between an input side and an output side of channel 20. Since the approximate outside diameter of target particle 35 is larger than the diameter of lumen 25, with the fluid flow traversing along the channel as shown by arrow 30, lumen 25 is occluded. When occluded, fluid flow in channel 20 ceases. With continued application of the pressure differential, such as for example, in an attempt to re-establish the flow, under some circumstances, target particle 35 will distort and possibly rupture.

Channel 20 is shown to have a circular cross section and is sometimes referred to as a zero-dimensional channel. A zero-dimensional channel has a pore with a diameter (or mean diameter in the case of filters based on cross-linked or highly branched matrices) smaller than the dimensions of the object intended to block, and thus mechanically prevents an object of diameter larger than that of the channel from traversing through the channel. The entrance of the channel becomes enriched with the excluded object and the fluid passing through the channel, which is sometimes referred to as the filtrate, becomes devoid of the excluded object, thus accomplishing isolation of the object, separation of the object from the filtrate, and concentration of the object near the entrance.

FIG. 1B illustrates channel 100A having a cross-sectional geometry according to the present subject matter which also provides mechanical exclusion of target particle 35 in fluid flow direction indicated by arrow 110. In the figure, channel 100A is sometimes referred to as a one-dimensional channel. A one-dimensional channel has an aperture cross sectional geometry such that a chord of length larger than the diameter of the object to be excluded can be drawn. In addition, the cross-sectional geometry also has a chord of length less than the width of the object. For example, in the figure, channel 100A has a rectangular exterior configuration and uniform wall thickness, thus forming rectangular aperture 105. Aperture 105 has a diameter, as denoted by dimension 120, and a width, as denoted by dimension 115. Target particle 35 has an average diameter denoted by dimension 37. As illustrated, width dimension 115 is smaller than dimension 37, and thus, particle 35 is precluded from passing through channel 100A. With target particle 35 lodged in the constriction formed by the dimensional difference between width dimension 115 and diameter dimension 37, fluid flow in channel 100A is allowed to continue since diameter dimension 120 is larger than diameter dimension 37. Fluid bypasses the constriction and passes around target particle 35 in the presence of continued application of a pressure differential. Pressure build-up on the surface of target particle 35 remains relatively low since fluid is allowed to bypass.

Figure 1C:
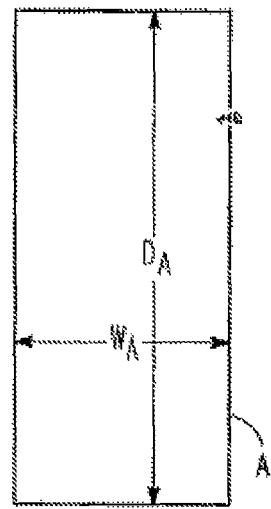
FIG. 1C illustrates an aperture of rectangular configuration.
Figure 1D:
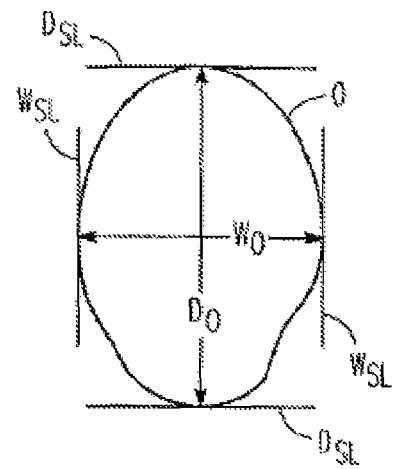
FIG. 1D illustrates an arbitrary object.

FIGS. 1C and 1D illustrate channel geometries in accordance with the present subject matter. FIG. 1C illustrates aperture A having cross sectional geometry in the form of a rectangle. Dimension $D_A$ represents a diameter of the aperture and dimension $W_A$ a width of the aperture. The width represents a minimum distance that can be drawn between two parallel supporting lines. The supporting lines are tangents of the perimeter. The diameter represents a maximum distance that can that can be drawn between two parallel supporting lines. In the case of the rectangular shaped aperture, the supporting lines are co-linear with the sides of the aperture.

FIG. 1D illustrates arbitrary object O having width denoted by $W_O$ and diameter denoted by $D_O$ for a particular cross section, defined as the minimum and the maximum distances, respectively, that can be drawn between two parallel support lines. In the case of object O, the diameter supporting lines are denoted $D_{SL}$ and the width supporting lines are $W_{SL}$.

Figure 1E:
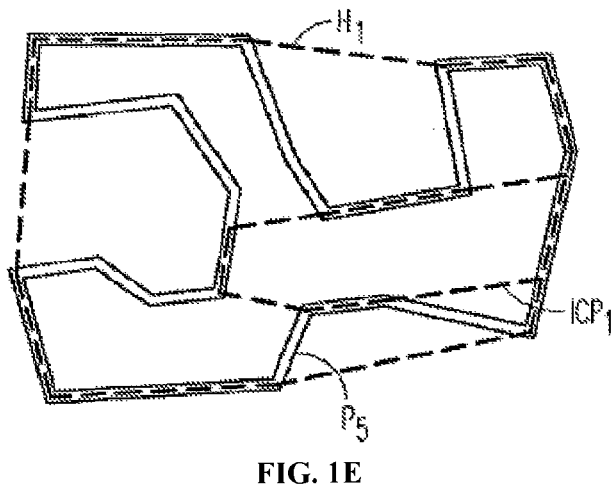
FIGS. 1E and 1F illustrate concave apertures.
Figure 1F:
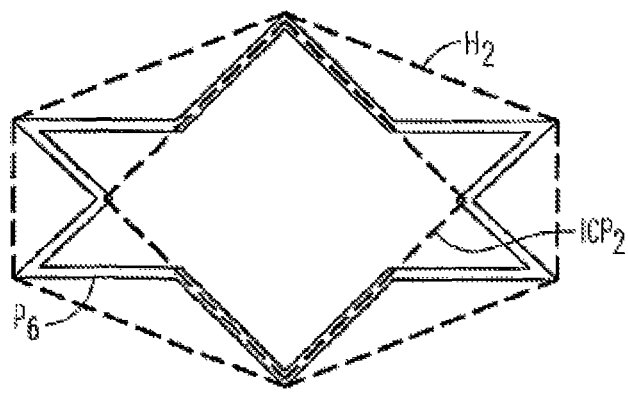
Figure 1G:
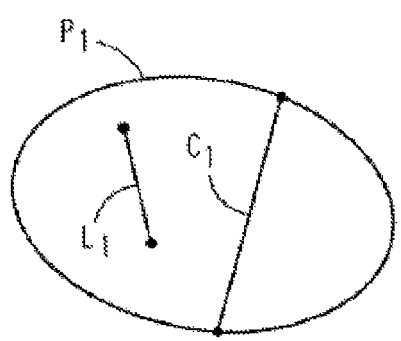
FIGS. 1G, 1H, and 1J illustrate apertures.

Aperture A will exclude object O when, for a particular cross section, $W_O$ is greater than $W_A$. Aperture A has cross sectional geometry that can be described as convex. A shape is convex if it wholly contains the straight line that joins any two points inside the shape. FIG. 1G illustrates convex shape P.sub.1 in which line segment L.sub.1 denotes a representative line segment having points that lie entirely within the perimeter of shape P.sub.1.

According to the present subject matter, a one-dimensional channel (having an aperture with convex cross sectional geometry) can be described as a channel wherein the aperture width is smaller than the width of the object to be excluded and the aperture diameter of the channel is larger than the diameter of the object as well as larger than the width of the aperture. A channel of circular aperture, wherein the aperture diameter is equal to the aperture width, is not considered as a one-dimensional channel.

Figure 1H:
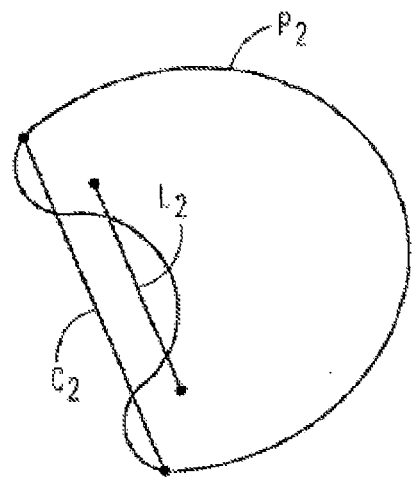
Figure 1J:
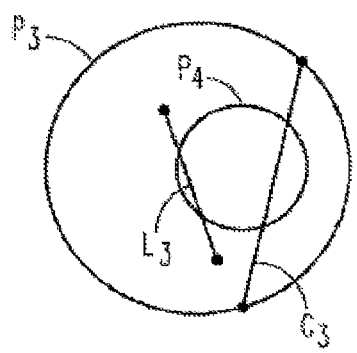

More generally, the present subject matter includes a channel having an aperture cross sectional geometry such that a chord of length larger than the diameter of the object to be excluded can be drawn. A chord is a straight line formed between two points on the perimeter of the shape. A chord may cross the perimeter. In other words, a chord may pass through the region enclosed by the perimeter as well as the region outside of the perimeter. FIGS. 1G, 1H and 1J illustrate exemplary shapes having chords $C_1$ (perimeter $P_1$), $C_2$ (perimeter $P_2$) and $C_3$ (perimeters $P_3$ and $P_4$), respectively.

The shapes illustrated in FIGS. 1H and 1J can be described as non-convex or concave. A shape is concave, or non-convex, if it has the property that the line segment connecting any two interior points is not totally contained in the shape. The shapes illustrated in FIGS. 1H and 1J, for example, are concave since line segments $L_2$ and $L_3$, respectively, can be drawn such that they cross the boundaries or perimeters of the shape.

According to the present subject matter, a one-dimensional channel (having an aperture with concave cross sectional geometry) can be described as having an aperture which features an inscribed convex polygon of a width smaller than the width of the object to be excluded and also a convex hull that has a diameter larger than the diameter of the object to be excluded. Inscribed means to construct a geometric shape inside another so they have points in common but the inscribed shape does not have any part of it outside the other. A convex hull is the smallest circumscribed convex shape that encloses an interior non-convex shape. Circumscribe means to construct a geometric shape outside another so they have points in common but the circumscribed shape does not have any part of it inside the other. FIGS. 1E and 1F illustrate exemplary concave apertures having perimeters $P_5$ and $P_6$, respectively, and inscribed polygons $ICP_1$, and $ICP_2$, respectively and convex hulls $H_1$ and $H_2$, respectively.

Figure 2A:
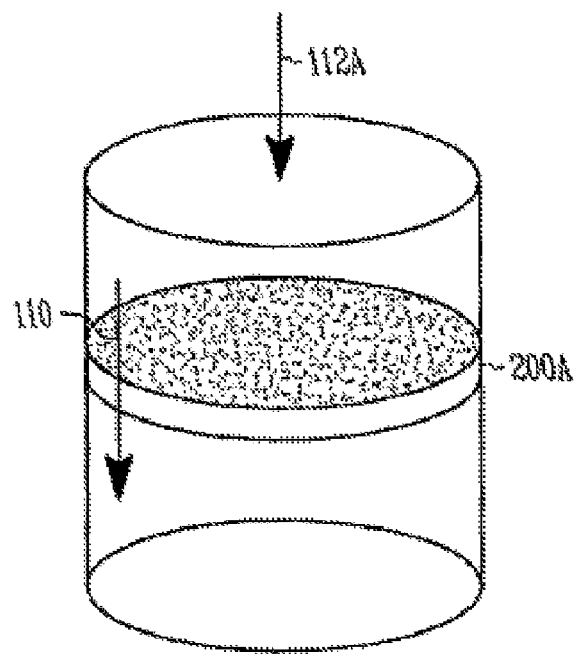
FIG. 2A illustrates a substrate having an axial flow configuration.
Figure 2B:
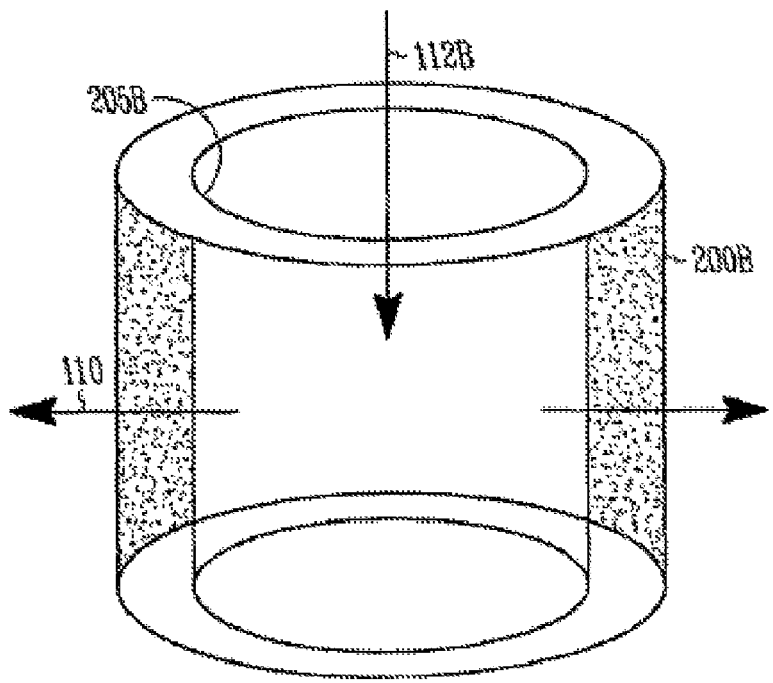
FIG. 2B illustrates a substrate having a radial flow configuration.

FIGS. 2A and 2B illustrate ways that a channel or an array of channel(s) can be configured in relation to a main flow direction. FIG. 2A illustrates substrate 200A configured for axial flow wherein the fluid flow enters in the direction denoted by arrow 112A and passes through the substrate in the direction denoted by arrow 110. The fluid flow, sometimes referred to as the filtrant, is substantially parallel to, or in the same direction as, the main fluid flow. In one example, substrate 200A includes a plurality of channels having one-dimensional geometry.

FIG. 2B illustrates substrate 200B configured for radial or lateral flow wherein the fluid flow enters along axis 112B and traverses the substrate in the direction aligned with arrow 110. Substrate 200B includes a plurality of one-dimensional channels. In a lateral flow configuration, as illustrated in the exemplary apparatus, the filtrant direction is substantially normal to the main flow. Lateral flow is sometimes referred to as cross flow.

The discussion regarding flow is merely exemplary. For instance, the fluid may be moved in a first direction to achieve a particular separation objective and later moved in a second direction to achieve a different objective. By way of example, the fluid flow may be reversed to dislodge the excluded objects from the channels or to isolate a particular object.

Figure 3A:
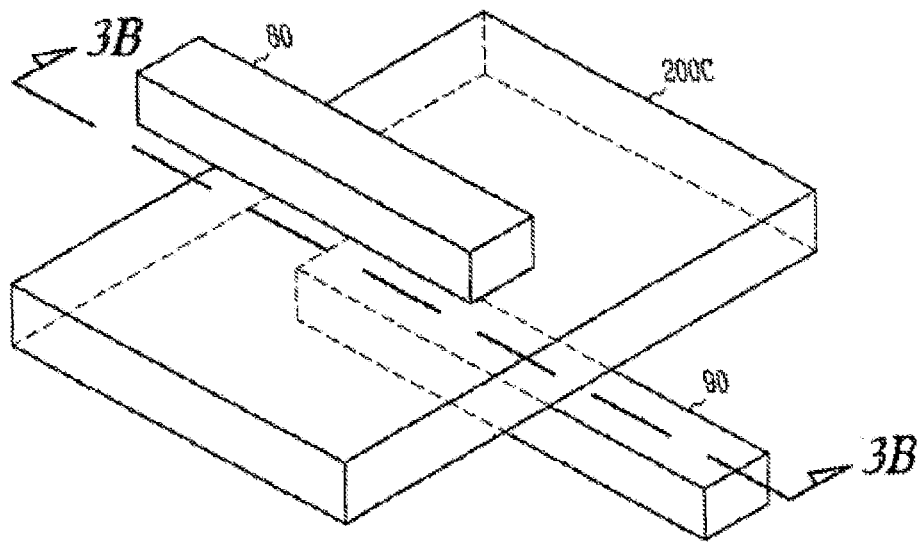
FIGS. 3A and 3B illustrate a substrate in the form of a membrane configured for axial flow.
Figure 3B:
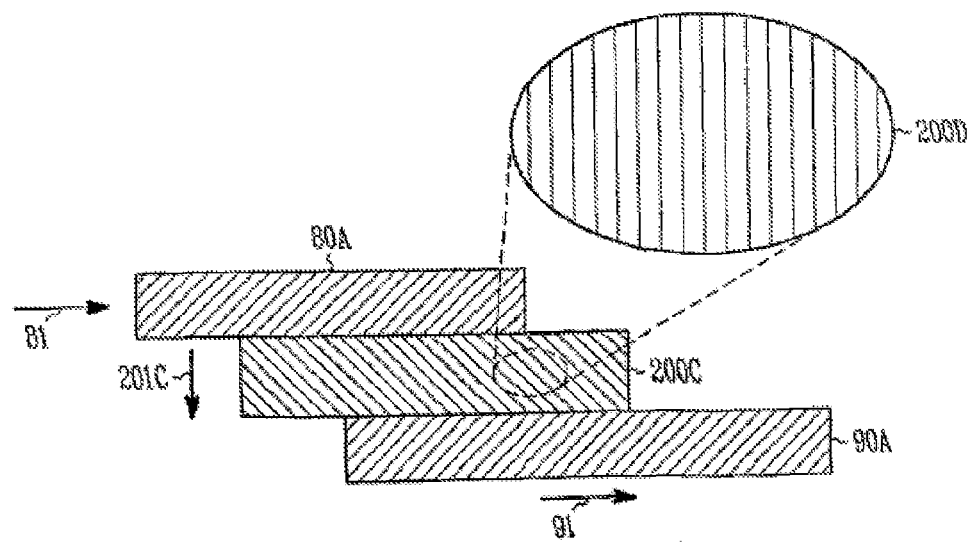

A one-dimensional channel or an array of one-dimensional channels may be employed within a subunit of a microfluidic device. FIGS. 3A and 3B illustrate an embodiment of one-dimensional channels (formed by sandwiching substrate 200C, which is fabricated with an array of one-dimensional channels as shown in 200D), between two substrates forming input conduit 80 and output conduit 90. Cut-away view 3B-3B is illustrated in FIG. 3B. Substrate 200C receives the filtrant via input conduit 80A and discharges the filtrate via output conduit 90A. Fluid flow in input conduit 80A is aligned with the direction of arrow 81, in substrate 200C aligned with the direction of arrow 201C and in output conduit 90A aligned with the direction of arrow 91. The structure of substrate 200C, when viewed with a side elevation, includes a plurality of channels, each of which is shown as a line in substrate 200D. The flow is in an axial configuration in the example illustrated; however the substrates and the embedded channels can be oriented for a lateral flow configuration. Various embodiments include an arbitrary number of input conduits and output conduits. In one example, a one-dimensional channel is fabricated directly in the top substrate or bottom substrate, thus eliminating the middle, or sandwiched, substrate.

Figure 4A:
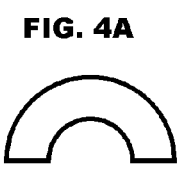
FIGS. 4A-4G illustrate various aperture cross sections.
Figure 4B:
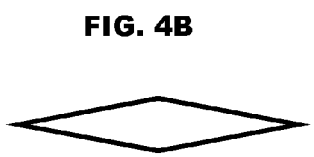
Figure 4C:
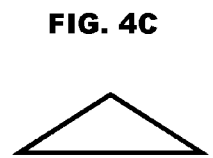
Figure 4D:
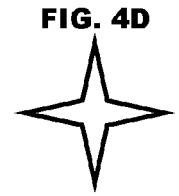
Figure 4E:
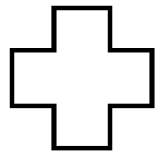
Figure 4F:
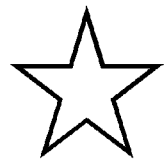
Figure 4G:
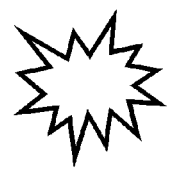

FIGS. 4A-4G illustrate a variety of aperture cross section geometries, each of which has an elongate portion (many having a polygonal shape) which can be configured in size and shape to capture a target particle in one region and allow passage of fluid in another region. For example, FIG. 4A shows an aperture having a section of a ring or a semicircular arc wherein an elongate portion includes a curved section. As such, a target particle will be lodged between the two curved surfaces of the aperture and fluid can continue to pass near one or both ends of the arc. FIG. 4B illustrates a diamond shaped aperture wherein the diamond is elongate and has two acute interior angles and two obtuse angles. The narrow portion of the aperture (nearest the obtuse angles) will capture the target particle and fluid will flow in the region of the acute angles. FIG. 4C illustrates a triangular aperture having one obtuse angle and two acute angles. The narrow portion of the aperture (nearest the obtuse angle) will capture the target particle and fluid will flow in the region of the acute angles. FIGS. 4D-4G illustrate star-shaped and cross-shaped apertures, each of which can be viewed as having more than one elongate portion. FIGS. 4D, 4F and 4G can be viewed as combinations of triangle-shaped or diamond-shaped apertures and FIG. 4E can be viewed as a combination of rectangular-shaped openings.

In addition to those shown, other apertures are also contemplated including, for example, a combination of the illustrated shapes. For example, an aperture can include an oval or an elongate circular shape or a segment of a circle having a flat on a side (shaped like the letter D). Furthermore, a particular substrate can have apertures of more than one shape or more than one particular size.

Figures 5, 6:
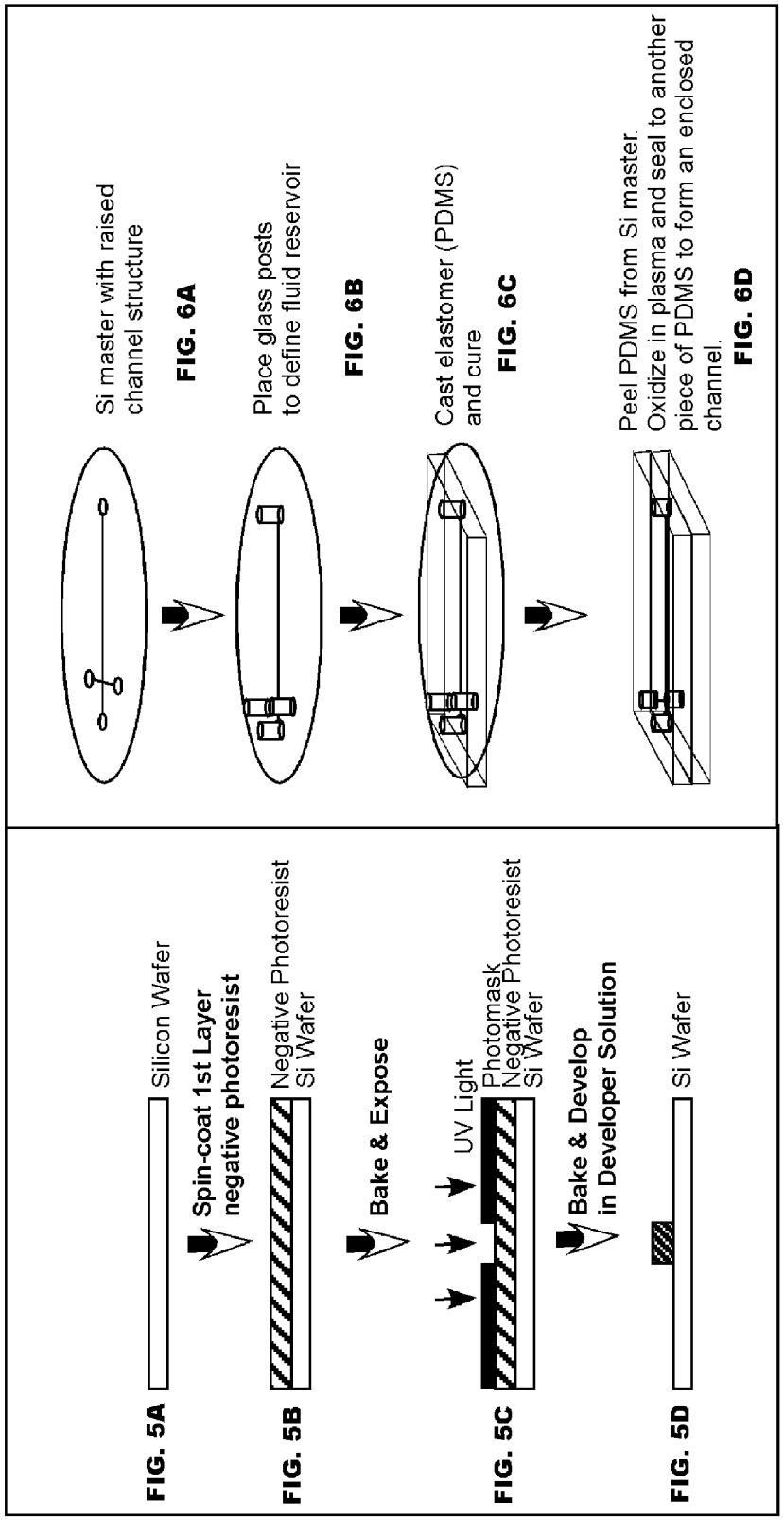
FIGS. 5A-5D illustrate a sequence for fabricating an exemplary device.
FIGS. 6A-6D illustrate a sequence for fabricating an exemplary device.

FIGS. 5A-5D, as well as FIGS. 6A-6D, illustrate an exemplary procedure for micro fabricating one embodiment of a chip according to the present subject matter. FIGS. 5A-5D illustrate production of a molding master on a silicon wafer from which polydimethylsiloxane (PDMS) slabs incorporating an array of one-dimensional channels can be replicated. In FIG. 5A, a negative photoresist is spun onto a silicon wafer. The photoresist is baked and then partially exposed to ultraviolet light through a patterned photomask using a mask aligner as shown in FIGS. 5B-5C. The portion of the photoresist layer exposed to ultraviolet light is cross-linked by the radiation, and becomes insoluble in the developer solution. Exposing the photoresist layer to the developer solution, in FIG. 5D, removes uncross-linked photoresist and leaves raised structures of cross-linked photoresist on the surface of the silicon, essentially a negative relief image of the original photomask. The application of photoresist, ultraviolet light exposure, and development in developer solution may be repeated to create multi-level layered structures. Upon completion of the desired topography, the resulting master mold is passivated with fluorosilane to allow a PDMS slab be cast on the master mold and removed. In an alternative method, positive photoresist layers are used to create positive, relief images. In one method, microstructures are produced directly in silicon or other substrate materials by etching with reactive chemicals in gaseous or liquid phase, by ablating with focused laser beams, or by bombarding with directed charged particle beams such as ions, electrons or plasma.

FIGS. 6A-D illustrates the production of a PDMS microfluidics device using a master mold. The master mold is produced by photolithography and by additional surface modifications in FIGS. 6A-B. In FIG. 6C, liquid PDMS is poured onto the surface of the master mold and baked to cure the liquid PDMS into a soft, semi-solid slab. In FIG. 6D, the cured PDMS slab is peeled from the master mold, oxidized in an oxygen plasma, and then bonded against another piece of PDMS slab to form enclosed channels. In one method, the cured PDMS is peeled from the master mold and bonded to a substrate of material such as glass, quartz, or silicon. In one method, a curable thermoset or photocurable polymer, such as thermoset polyester, polycarbonate, or polymethylmethacrylate, is used in place of PDMS following a casting-replication process. In one method, the aforementioned microstructures are directly produced in a substrate by chemical etching, laser ablation, or charged particle bombardment and bonded to another substrate to form an enclosed fluidic channel.

Figure 7:
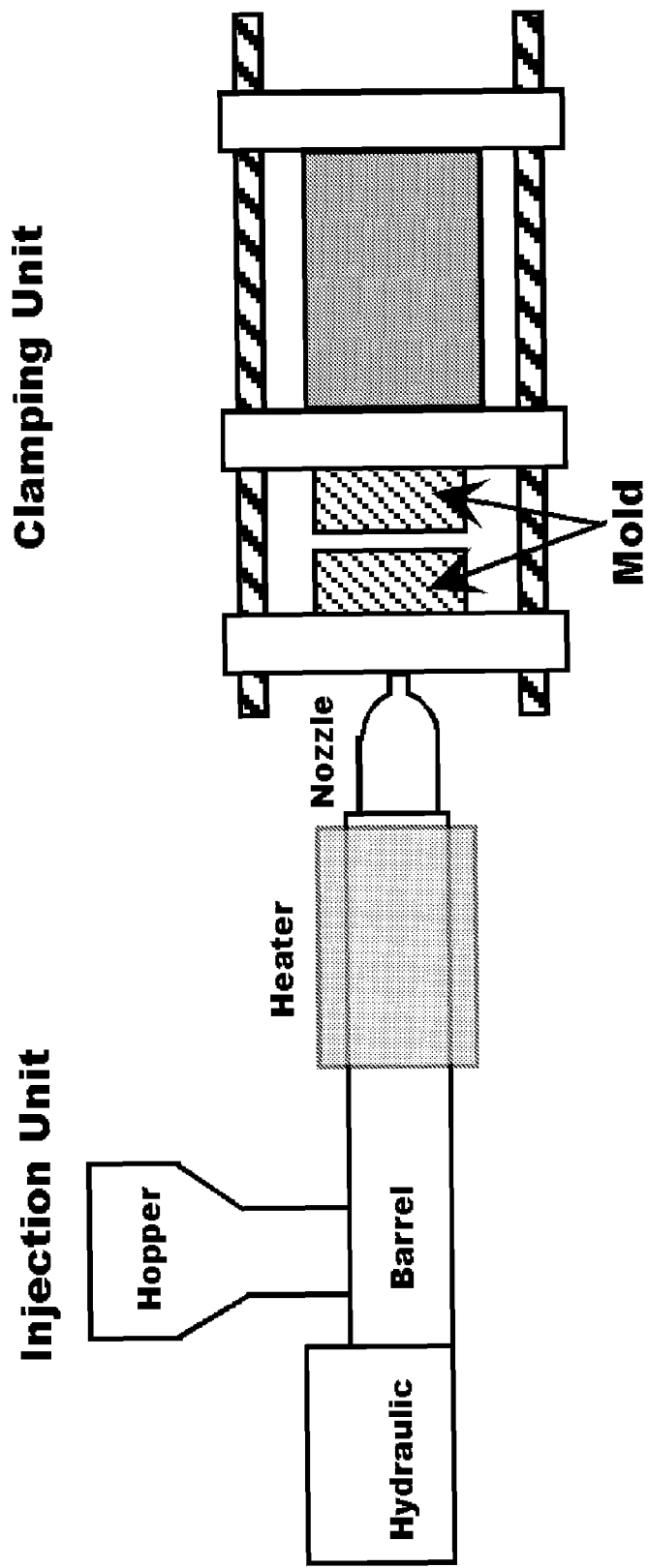
FIG. 7 illustrates an injection molding system for fabricating and replicating an exemplary device.

FIG. 7 illustrates an exemplary method to replicate microfluidic chips by injection-molding of thermoplastic materials. Solid plastic pellets are loaded into the hopper and softened under hydraulic pressure and temperature. The liquified material is then injected into a master mold with channel features. Upon cooling the plastic replica solidifies and is removed and bonded to another substrate to form an enclosed fluidic device.

Figure 8:
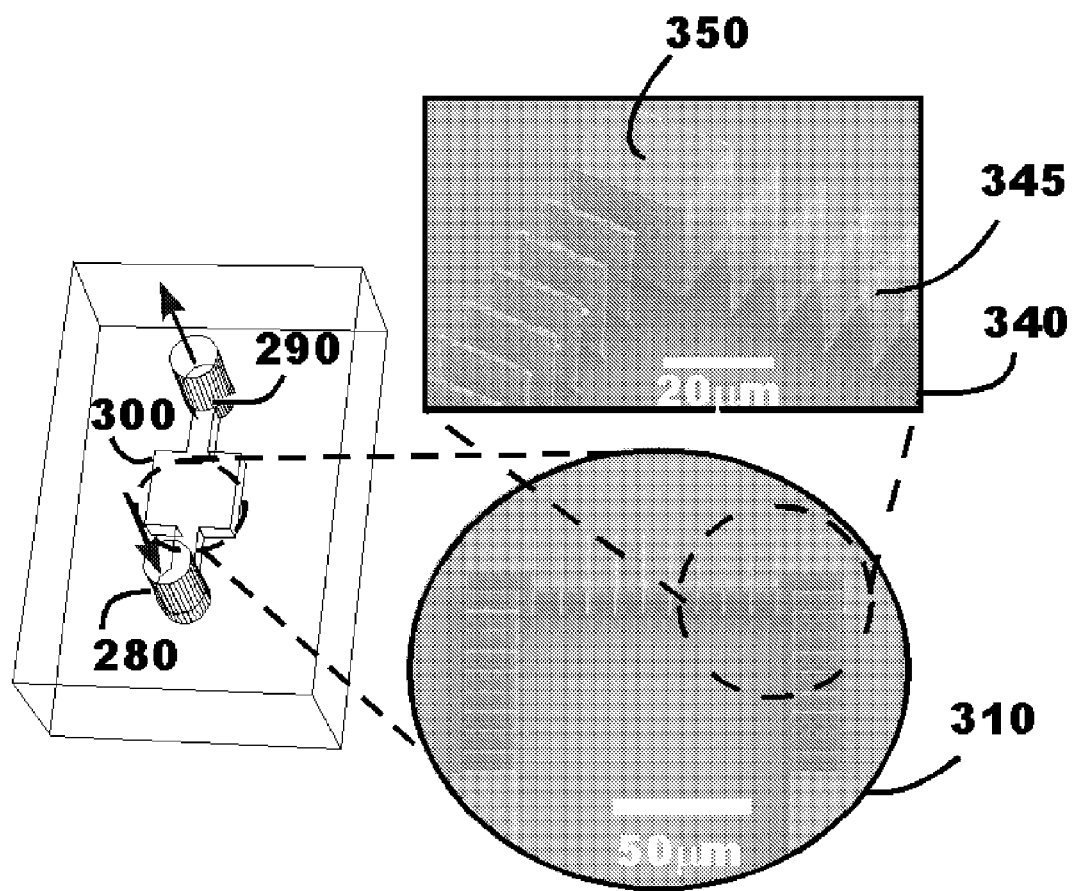
FIG. 8 illustrates scanning electron microscopy images of an exemplary device.

FIG. 8 illustrates scanning electron microscope images of exemplary device 300. Fluid flow is aligned with the direction illustrated by the arrows and enters at inlet 280 and exits at outlet 290. In particular, enlargement 310 and enlargement 340 each illustrate a plurality of thin channel walls 345 aligned in a pattern having "corner elements" 350. One-dimensional channels (3 µm aperture width by 20 µm aperture diameter by 20 µm channel axial length) are formed between thin channel walls 345 as well as between thin channel walls and corner elements 350. Analytes or biofluids are introduced into device 300 via inlet 280 by the hydrostatic pressure difference due to the difference in liquid height between inlet 280 and outlet 290. The channel surfaces may be modified chemically to enhance wetting or to assist in the adsorption of select cells, particles, or molecules.

Device 300 can be used to separate a subpopulation of cells from whole blood. Whole blood includes a complex mixture of white blood cells (leucocytes), red blood cells (erythrocytes), platelets, and plasma. Leucocytes are spherical-shaped with diameters ranging from 6 µm to 20 µm and are not easily deformed as they contain subcellular compartments such as nucleus and organelles. Erythrocytes, on the other hand, are disc-shaped fluidic sacs with nominal diameter of 7 µm and height of 2 µm. Because erythrocytes contain mostly fluids and have an extremely flexible cytoskeleton designed to support high degrees of deformation, they can be deformed easily and pass though constrictions even smaller than their smallest dimension. The use of one-dimensional channels provides mechanical exclusion to leucocytes in one dimension and leaves open areas or bypass regions next to the trapped or captured leucocytes such that the filtrate or carrier fluid can continue to flow. An erythrocyte can pass though a one-dimensional channel in a sideways mode.

Figure 9A:
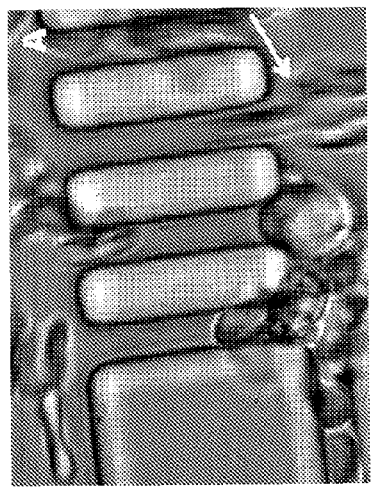
FIGS. 9A-9F illustrate the cell separation and enrichment operations of an exemplary device.
Figure 9B:
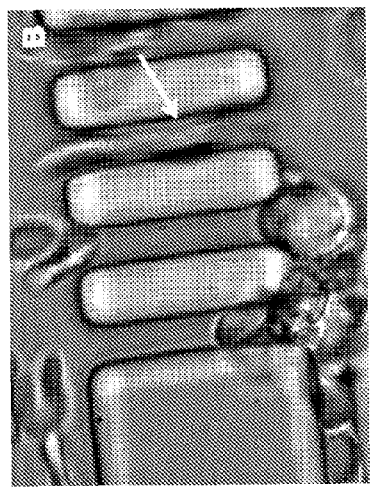
Figure 9C:
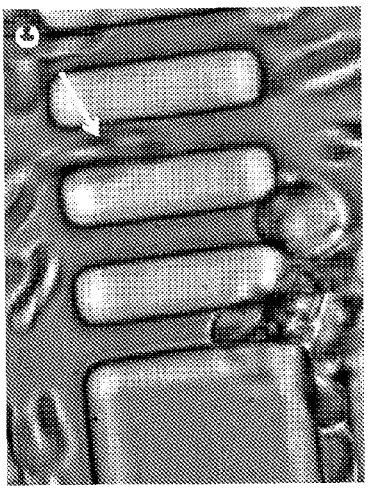
Figure 9D:
Figure 9E:
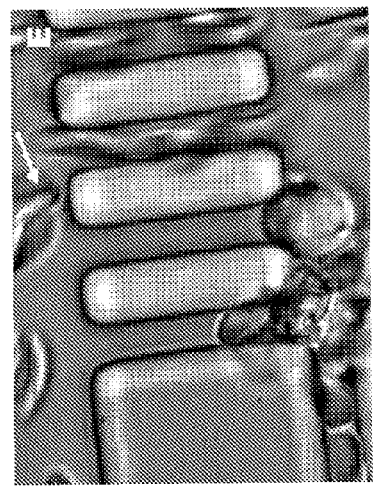
Figure 9F:
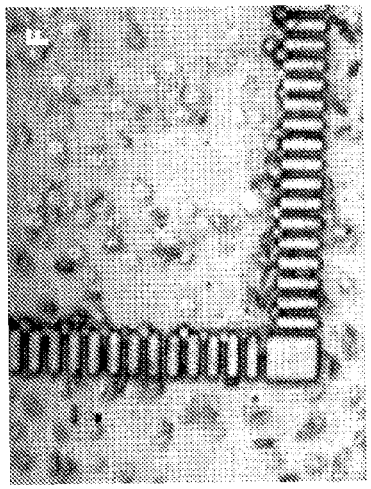
Figure 10A:
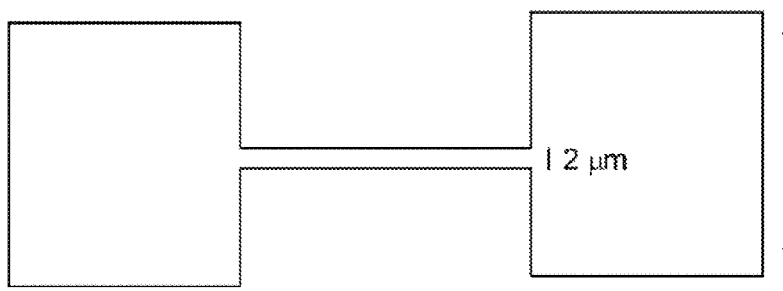
FIGS. 10A and 10B illustrate top and side elevation views of a zero-dimension channel.
Figure 10B:
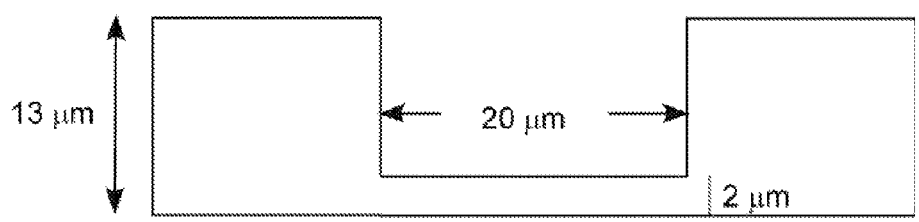
Figure 10C:
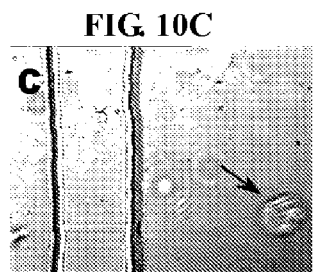
FIGS. 10C-10H illustrate a cell lysing event by flowing a biofluid containing cells through a zero-dimensional channel.
Figure 10D:
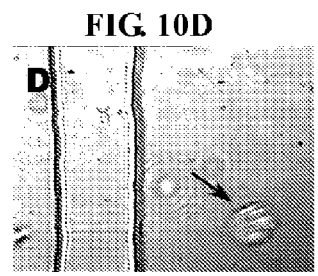
Figure 10E:
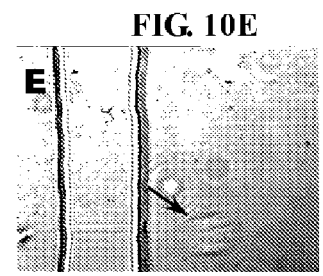
Figure 10F:
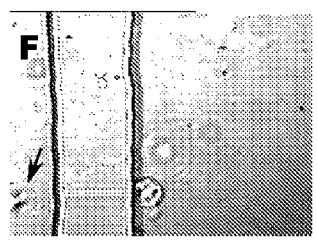
Figure 10G:
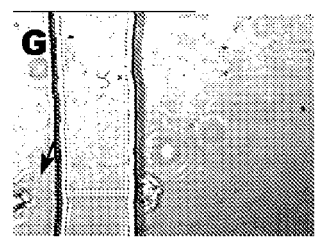
Figure 10H:
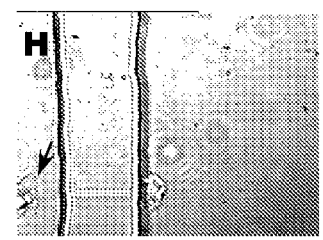

The following exemplary procedure can be used to separate leucocytes from whole blood using device 300. A 0.05 ml drop of human whole blood is added to approximately 0.2 ml isotonic phosphate-buffered saline (PBS) solution containing 1.5 mg/ml of K.sub.3 EDTA as anticoagulant, 0.1 M of PBS, and 0.15 M of NaCl. Approximately 1 µL of this mixture is pipetted into the inlet reservoir of the device and additional buffer is added on top of the fluid reservoir to ensure steady gravity-driven flow. FIGS. 9A-9F show a sequence of photographs documenting the exclusion of leucocytes from whole blood mixture using device 300. As the mixture is passed through device 300, leucocytes (circular objects at the opening of each channel in the lower center and lower left corners of FIGS. 9A-9E) are unable to pass though the one-dimensional channels and accumulate near the channel entrances. However, since the aperture diameter is greater than the diameter of a leucocyte, the leucocytes do not block the flow completely and consequently the leukocytes remain undamaged and intact. Erythrocytes, however, are free to flip or deform while traversing through a one-dimensional channel. The white arrows in FIGS. 9A-9E indicate the trajectory of an erythrocyte moving through a one-dimensional channel by flipping onto its side. FIG. 9F shows a larger area of device 300 during the cell separation operation, where leucocytes (white circular objects) can be seen accumulating at more than 90% of channel entrances while erythrocytes passing freely through the channels. The inlet side of device 300 corresponds to the upper right corner of FIG. 9F.

A leucocyte-separation experiment can be conducted with a zero-dimensional channel, as illustrated in FIG. 10, for purposes of comparison. FIGS. 10A and 10B show the top and side elevation views of a channel having a square cross section of 2×2 μm and an axial length of 20 μm coupled to input and output chambers, each having dimensions of 100× 13 μm. Identical preparation method is used to prepare the blood mixture and a syringe is used to deliver the mixture into the inlet chamber. FIGS. 10-10H show a sequence of images of a leucocyte (marked by arrows) approaching the channel and completely blocking the channel, and having partially expelled its contents under the applied pressure. A leucocyte blocking the zero-dimensional constriction forms a complete blockage and the separation function ceases once the fluid flow is precluded.

Figures 11A, 11B, 11C:
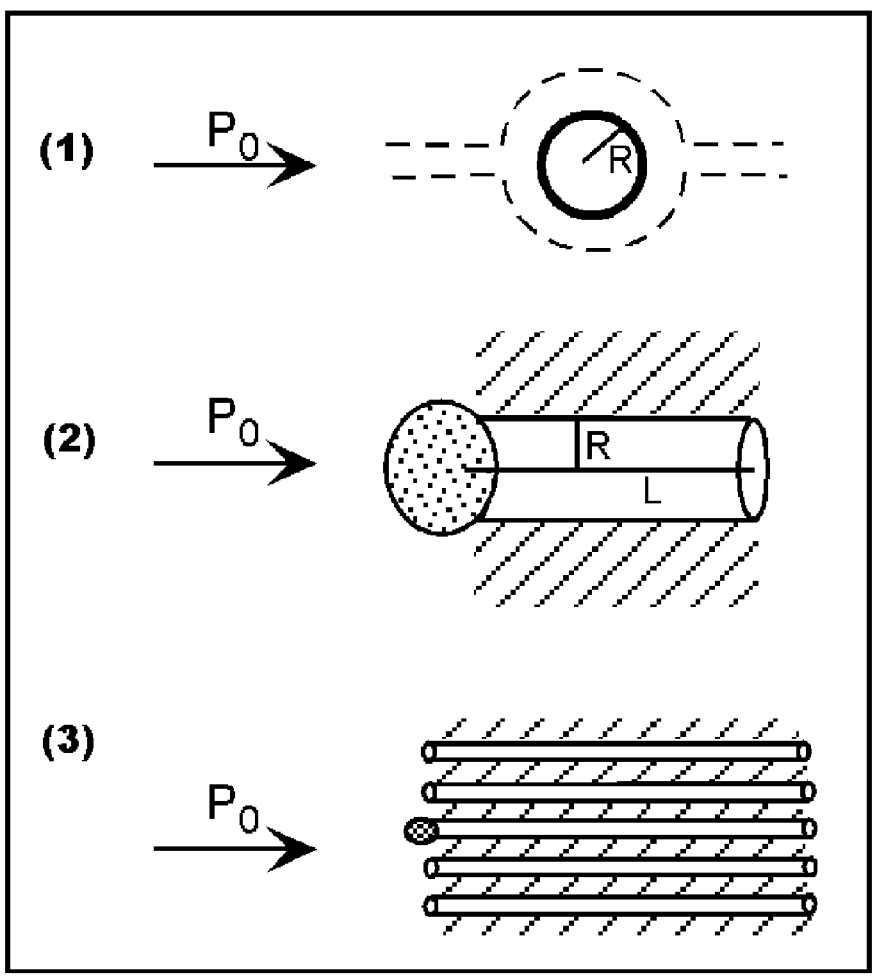
FIGS. 11A-11C illustrate various scenarios that a biological cell or particle can experience pressure forces.

A theory as to the physics of channel blockage in relations to the local pressure experienced by cells is illustrated in FIGS. 11A-11C, 12, 13, 14A, 14B, 15A and 15B. FIGS. 11A-11C illustrates various scenarios that can affect the local pressure experienced by a biological cell in separation processes. FIG. 11A illustrates the hydrodynamic pressure imparted by a carrier fluid as it flows past a cell. FIG. 11B illustrates the pressure experienced by a cell completely clogging a single channel. FIG. 11C illustrates the pressure experienced by a cell clogging a channel in the presence of multiple parallel channels available for flow bypass. As discussed herein, a one-dimensional channel provides improved performance relative to that of a zero-dimensional channel in terms of reducing cell lysing since a one-dimensional channel permits the carrier fluid to flow past the trapped cells and reduce the pressure escalation associated with the complete blockage of a zero-dimensional channel.

Figure 12:
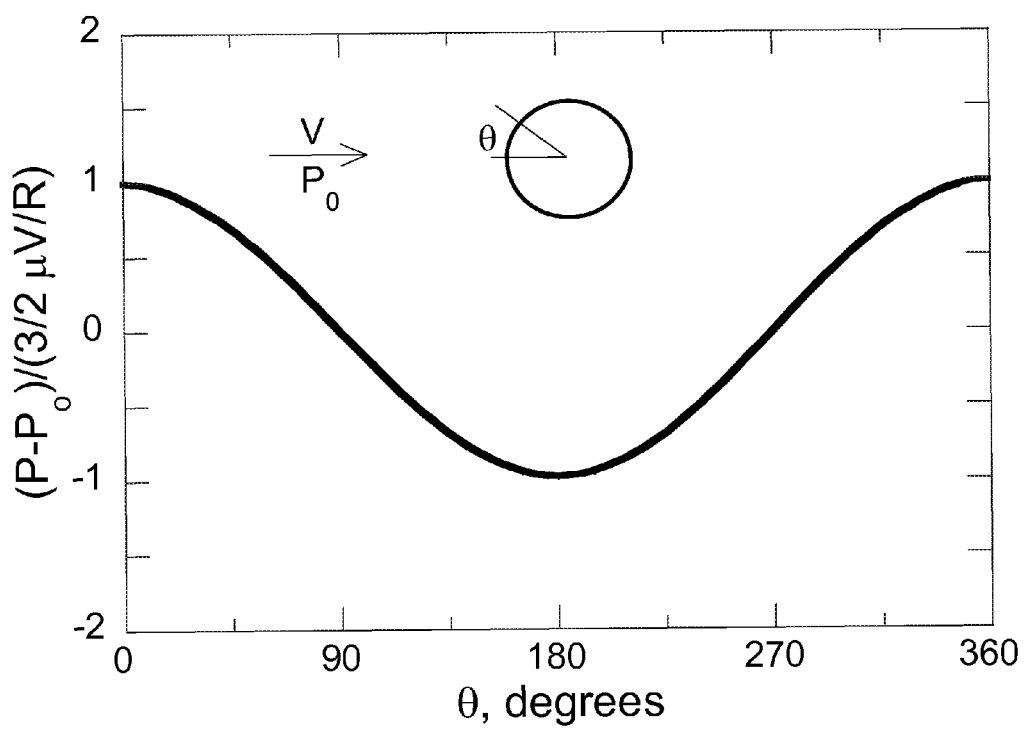
FIG. 12 illustrates the pressure distribution around a free spherical particle in a flow.

FIG. 11A illustrates pressure encountered by a single cell in flow. The pressure experienced by a cell in a separation environment depends strongly on whether the carrier fluid is able to pass around the cell. When a cell is excluded by a one-dimensional channel, the fluid is still able to flow around the cell, and thus the pressure is essentially the same as if the cell is a free particle in the flow. The upstream half of the cell experiences a higher pressure from the direct impingement of fluid, which leads to a local distribution of pressure around the cell (P) given by:

$$P = P_0 + \frac{3}{2}\frac{\mu V}{R}\cos\theta \qquad \text{Eq. (1)}$$

where $P_0$ is the upstream pressure (for convenience, the downstream pressure is assumed to be 0), μ is the viscosity of the carrier fluid, R is the radius of the cell, and V is the velocity of the fluid. The angular distribution of the pressure from Eq. (1) is plotted in FIG. 12. FIG. 12 shows pressure distribution from a flow around a spherical object where zero degree is defined as the angle opposite of the upstream flow direction.

The maximum pressure difference ($\Delta P_{max}$) between 0° (fluid impinging) and 180° (wake) is given by:

$$\Delta P_{max} = 3\frac{\mu V}{R} \qquad \text{Eq. (2)}$$

Figure 13:
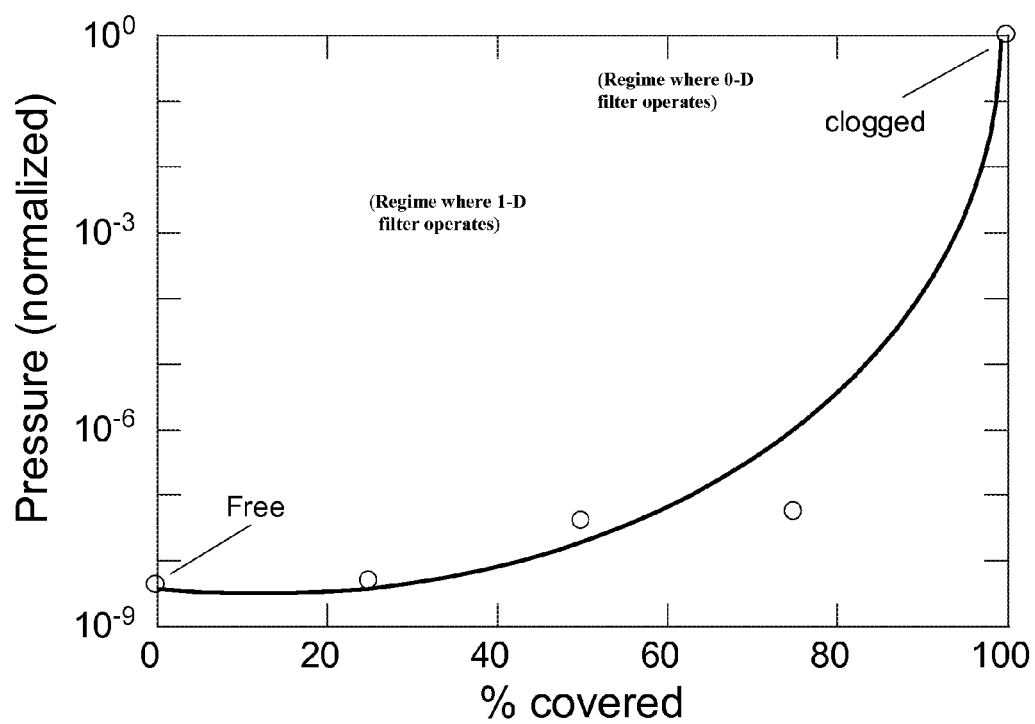
FIG. 13 illustrates the pressure experienced by a cell lodged at a separation channel entrance as a function of the percentage of channel cross-sectional area blocked.

FIG. 11B illustrates a cell clogging a single channel. In the case where the cell completely clogs a zero-dimensional channel (or pore), the carrier fluid is unable to recombine behind the cell and the pressure across the cell is simply the same as the externally applied pressure differential (i.e. the syringe pump pressure.) The externally applied pressure differential is always larger than the pressure difference from the flow around a cell (e.g. when a cell is trapped by a one-dimensional channel), sometimes by several orders of magnitude, because the former is what is required to drive the flow through the entire filter and the latter is only a small pressure drop from the fluid wrapping around a cell. For a partially clogged channel, some fluid is allowed to pass by the cell and relieve the pressure difference across the cell. The degree of relief is related to the unobstructed cross-sectional area available for flow. FIG. 13 shows the effect on the cell pressure as a cell covers the channel opening. In other words, FIG. 13 illustrates cell pressure as a function of the percent of channel area blocked. Data points were obtained by solving the Navier-Stokes equation numerically for a 5 μm (diameter) by 10 μm (axial length) cylindrical channel partially blocked by a 5 μm (diameter) cell.

FIG. 11C illustrates clogging of one channel in an array of multiple parallel channels. In cases where systems of unclogged parallel channels are available to allow the carrier fluid to bypass and recombine at the exit side of the filtration area, the pressure experienced by the clogged cell is equivalent to the pressure drop across the unclogged parallel channels. For one unclogged parallel channel, the pressure drop from viscous dissipation ($\Delta P_{channel}$) is given by the Poiseuille equation:

$$\Delta P_{channel} = \frac{32\mu VL}{D^2} \qquad \text{Eq. (3)}$$

where μ is the viscosity of the carrier fluid, D is the diameter of the channel, L is the axial length of the channel, and V is the velocity of the fluid.

For n parallel channels, the pressure drop is reduced by a factor n, since more cross-sectional area is available for flow:

$$\Delta P_{n-channel} = \frac{32\mu VL}{nD^2} \qquad \text{Eq. (4)}$$

A comparison of this pressure drop to the pressure of a trapped cell in a one-dimensional channel (Eq. (2)) can be made by making simplifying assumptions. Assume that the axial length of the pore is at least five times the pore diameter (L=5D) and that the diameter is twice the radius of the channel (D=2R) in Eq. (4). Accordingly, the results are given by:

$$\Delta P_{n-channel} = \frac{32\mu V(5(2R))}{n(2R)^2} = \frac{80}{n}\frac{\mu V}{R} \qquad \text{Eq. (5)}$$

A comparison of Eq. (5) with Eq. (2) reveals that n, the number of unclogged bypass channels, should be approximately 80/3 or 27 in order to relieve the pressure of one clogged channel to the point of equivalent to cell trapping by a one-dimensional channel. In other words, if more than 4% of the total channels are clogged in a substrate consisting of purely zero-dimensional channels, then the remaining unclogged channels become less effective than a single one-dimensional channel in terms of circumventing the pressure build-up. This poses a capacity issue when devices based on zero-dimensional channels are used to isolate cells.

Thus, an increased probability of cell lysing arises from having a multitude of zero-dimensional channels. The pressure experienced by the cell is directly related to the tension on the cellular membrane. In other words, the pressure differential forces the cell to stretch, and when the increase in surface area exceeds 2-4% of the original surface area, the cell is lysed.

Figure 14A:
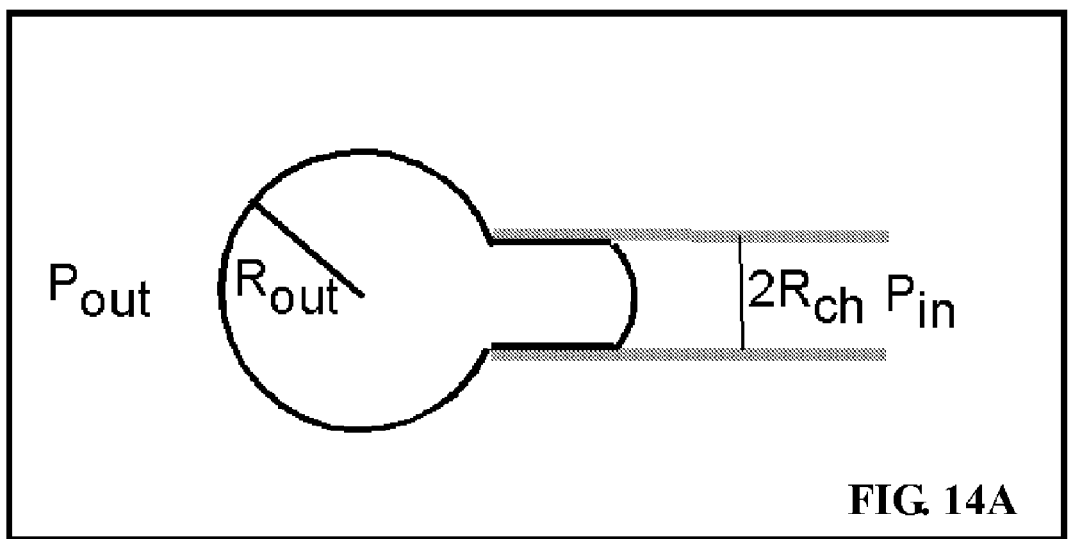
FIG. 14A illustrates cellular membrane deformation as a result of a cell lodged at a pore subject to applied pressure differential.

FIG. 14A illustrates a channel of diameter $2R_{ch}$ completely clogged by a cell with the external diameter $R_{out}$. In the simplified geometry shown in FIG. 14A, the pressure required to sustain curvature to the membrane tension is by Laplace's law:

$$\Delta P = 2\tau \left( \frac{1}{R_{ch}} - \frac{1}{R_{out}} \right) \qquad \text{Eq. (6)}$$

where $\Delta P$ is the pressure difference between the outside ($P_{out}$) and the inside ($P_{in}$) of the channel, $R_{ch}$ is the radius of curvature inside the channel, $R_{out}$ is the radius of curvature of the remaining cell volume outside of the channel, and $\tau$, the membrane tension, is proportional to the surface area change.

Figure 14B:
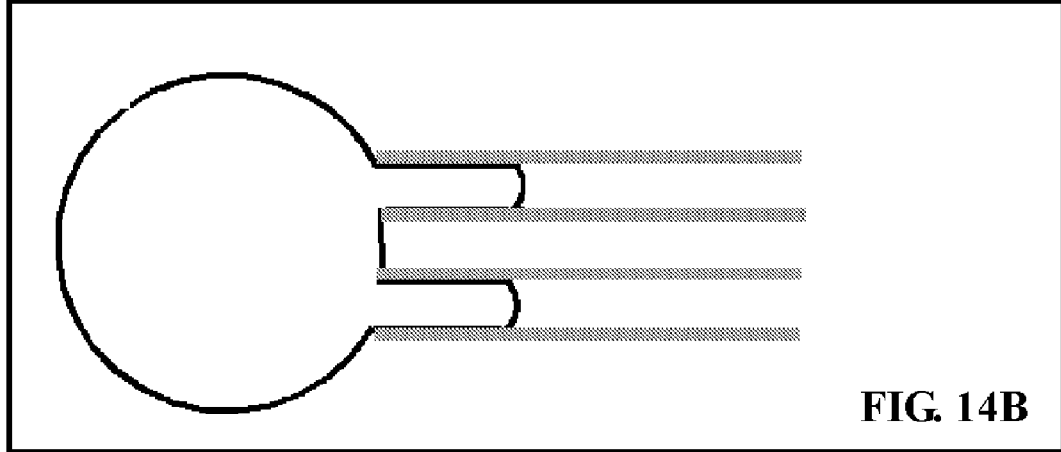
FIG. 14B illustrates cellular membrane deformation as a result of a cell lodged at two pores subject to applied pressure differential.

FIG. 14B illustrates two channels simultaneously clogged by a cell. In such a case, where a cell covers two pores simultaneously, the membrane tension is given by adding up the curvatures:

$$\Delta P_{2-pores} = 2\tau \left( \frac{1}{2r_{ch}} - \frac{1}{R_{out}} \right) \qquad \text{Eq. (7)}$$

From Eq. (7), it will be noted that for a constant pressure differential, if a cell covers more zero-dimensional channels (pores), the membrane tension $\tau$ will increase, and the probability of cell lysing increases. A difference between a one-dimensional channel and multiple closely packed zero-dimensional channels (pores, as analyzed above), includes the ability of one-dimensional channels to allow flow to pass around a cell in the same channel, keeping the pressure drop across the cell small, and thus minimizing damage to the trapped cell. In situations where a one-dimensional channel trap cells in high density, interstitial spaces between closely-packed cells are available for fluid flow, as illustrated in FIG. 15A. The zero-dimensional channels illustrated in FIG. 15B do not provide an interstitial space.

Separation, isolation, and enrichment of subpopulations of biological cells from a complex biofluid mixture may have clinical applications in disease diagnosis. The present subject matter can be used to detect alterations in cell populations as well as the presence of parasites or foreign matters in biofluids to facilitate diagnosis.

In one embodiment, an array of one-dimensional channels can be integrated into a diagnostic device to facilitate the collection and enrichment of leucocytes and malaria-infected erythrocytes in the diagnosis of malaria. Severe malaria is caused by the parasite Plasmodium falciparum. The parasite invades the erythrocytes in blood, and its maturation process causes the erythrocytes to lose deformability. The physical changes of invaded erythrocytes at the cellular level include the incorporation of knob-associated histidine-rich protein (KAHRP) in the cellular membrane, increased internal viscosity due to the parasite presence, and a more spherical surface-to-volume ratio. Microfluidic observations have provided visual confirmation that parasitized erythrocytes frequently result in capillary blockage, which has been proposed as the underlying pathogenesis mechanism.

Current diagnostic protocol for malaria diagnosis includes microscopic examination of blood smear and the visual identification of malarial parasites. Two microscopy procedures are recommended by the Center for Disease Control (CDC) and the World Health Organization (WHO): in thick smear preparation, erythrocytes are lysed, and a microscopist visually counts the number of parasites against the leucocytes present in 100 fields under 100× oil-immersion objective and converts the ratio accordingly; in thin smear preparation, erythrocytes are not lysed, and a microscopist examines 300 fields under the same magnification and counts the parasitized erythrocytes among normal erythrocytes.

The present subject matter can be applied to the field of malaria diagnostics. The apparatus can selectively isolate leucocytes as well as parasitized erythrocytes while allowing normal erythrocytes to pass though. The present subject matter also acts as a cell concentrator as the isolated cells accumulate in an enclosed volume, thus reducing the number of fields necessary to achieve the same cell counts compared to the thick smear protocol. In addition, one example of the present subject matter provides a reduced pressure drop across the substrate.

FIGS. 16A-16F illustrate a sequence of photographs showing trapping of malaria-infected red blood cells (RBC) and white blood cells (WBC) while allowing the passage of uninfected red blood cells using an exemplary device. One microliter of sample analyte, including malaria-infected human blood diluted with RPMI growth media to ~10,000 cells/μL is pipetted into the inlet. Additional growth media and dyes may be added to control the flow rate and improve the visualization of cells and parasites. In one example, the channel surfaces are modified chemically to improve trapping of desired cells. The exemplary device is then placed onto a Nikon TE300 inverted microscope and inspected under a 100× oil-immersion objective magnification. FIG. 16A shows three parallel one-dimensional channels of aperture dimensions 4 μm width by 16 μm diameter (channel height) and an axial length of 20 μm, formed between four rectangular walls. The fluid flow is from right to left and driven by the hydrostatic height difference between the inlet and outlet reservoirs (gravity-driven). Immediately adjacent to the channel entrances are one trapped leucocyte (white blood cell) and four infected erythrocytes (RBC). The malaria-infected erythrocytes are spherical and are unable to pass through the one-dimensional channels. Young *P. falciparum* parasites corresponding to the developmental stage of ring-stage trophozoite are visible in the form of a small white granule inside two of the infected erythrocytes. FIGS. 16A-16F show the unrestricted movement of an uninfected erythocyte (marked by black arrow) through a one-dimensional channel by flipping onto its side. Thus the entrance side of the one-dimensional channels becomes enriched with leucocytes and infected erythrocytes. These cells may be enumerated to document the parasite concentration and the developmental stages of the parasites may be accurately identified.

In addition to malaria, the present subject matter can be used for monitoring of CD4+ T-lymphocytes (CD4+ T-cells) in Human Immunodeficiency Virus (HIV) diagnostic and monitoring. The absolute CD4+ T-lymphocyte count can serve as a criterion to initiate antiretroviral therapy and opportunistic infection prophylaxis in HIV-infected patients. The reduction of CD4+ T-lymphocytes, which is a subpopulation of leucocytes (white blood cells), strongly correlates to the decline of the immunological defense. Monitoring of CD4+ T-lymphocytes (CD4+ T-cells) level every 3-6 months in all HIV-infected persons has been recommended by the CDC Public Health Service as a way to initiate appropriate treatment strategies and to evaluate treatment efficacy.

In some laboratories, the absolute CD4+ T-cell number is established using the product of three laboratory techniques: the total white blood cell count, the percentage of white blood cells that are lymphocytes, and the percentage of lymphocytes that are CD4+ T-cells. Single platform flow cytometers such as FACSCount (BD Biosciences) is commercially unavailable in some developing countries or as a portable device.

Low cost alternatives for CD4+ T cell monitoring include nonflow bead-based labeling methods with minimal microscope requirements such as magnetic Dynabeads (DynalBiotech ASA) and latex cytospheres (Beckman Coulter). Although the measurements from these methods in general correlated well with that from flow cytometry under experienced hands, due to increased manual handling and reading assay, inconsistent results can incur, as exemplified by a recent report that number of positive cell can depend on how vigorous the samples were shaken during reagent mixing.

The present subject matter can be used to remove erythrocytes and accumulate leucocytes prior to appropriate immunophenotyping to distinguish CD4+ T-lymphocytes from other leucocytes. Lymphocytes can be distinguished from other leucocytes (e.g. monocytes and granulocytes) on the basis of size, granularity, or morphology and the absolute distinction of CD4+ T-cell within lymphocytes can be accomplished via immunophenotyping. In manual counting methods such as aforementioned Dynabeads and Cytospheres, erythrocytes must be lysed with appropriate reagents so leucocytes can be clearly seen, since the ratio of leucocyte to erythrocyte in whole blood is 1:1000. Employing chemical lysing reagents, however, has been known to reduce CD4+ T cell counts by as much as 10% when compared to no-lyse methods because lysing agents can lead to destruction of the cell membrane as well as the epitopes for fluorescence labeling. This type of cell count reduction occurs nonuniformly among subclasses of leucocytes. In HIV monitoring, where falling T-cell count signals the progression of the disease, such erroneous reduction in absolute count can misguide the physicians in interpreting the progress of treatment.

In addition to the foregoing disease diagnostic applications, cancer-related rare cells can also be detected using the present subject matter. Tumor cells can exfoliate from solid tumors and transport throughout the body via the blood stream. These circulating tumor cells (CTCs) are present in extremely low concentration in the peripheral blood, estimated to be on the order of one tumor cell per $10^6$ to $10^7$ mononuclear cells, which is equivalent to one tumor cell per 0.5 ml to 5 ml of peripheral blood. At such low concentration, a sample with estimated 100 million cells must be screened in order to detect at least one CTC with 99.995% certainty. An automatic digital microscopy (ADM) scanning at a typical speed of 800 cells/second would require 18 hours to complete a sample that size, and even with an improved optical system, it is estimated that the scanning task would still require about one hour with additional manual examination.

The CTCs can be distinguished from normal cells by two physical characteristics: (1) tumor cells preferentially express cytokeratins as integral components of cytoskeletons, and as such may be distinguished by means of specific antibodies, and (2) most CTCs have whole cell areas 2.8 to 5.7 times larger than normal leucocytes. Current enrichment methods of CTCs can be divided into immunological-based approach (e.g. positive and negative immunomagnetic separation) and physical separation method (based on filtration using a polycarbonate filter with 8\μm pores). Using filtration, researchers have compared CTCs in patients with hepatocellular carcinoma before and during surgery, detected CTCs in peripheral blood of breast cancer patients and correlated to the disease stage, and found that spontaneous circulation of CTCs in peripheral blood is a sign of tumor progression and tumor spread in primary liver cancer patients, all with high sensitivity.

Since the size difference between cancerous cells and normal cells is considerable, the present subject matter can be used to isolate the circulating tumor cells from whole peripheral blood or spinal fluids and the system may be configured for inspection under a microscope without disassembling the filtration housing, and without concern of lysing the rare cancerous cells.

Figure 17:
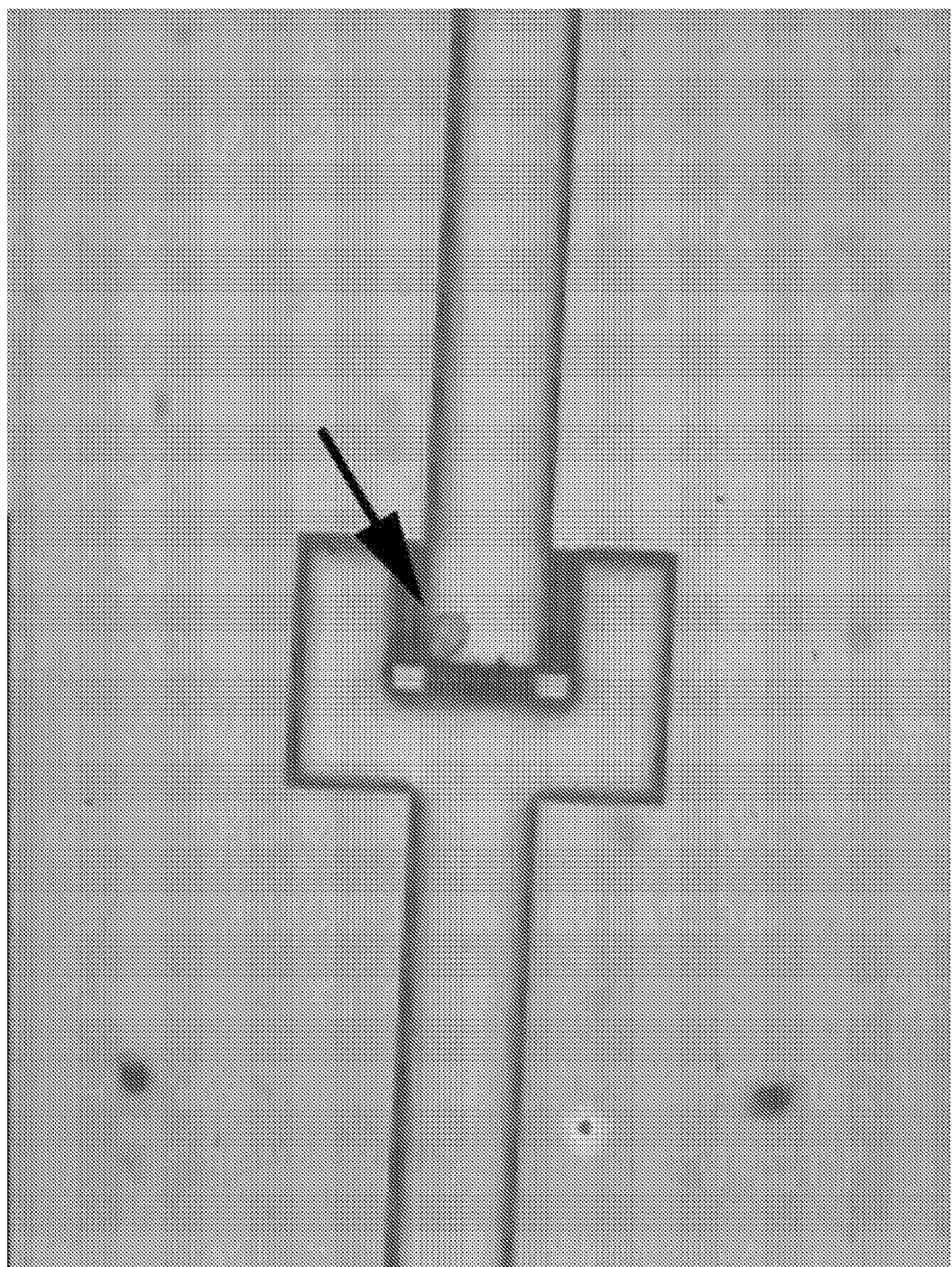
FIG. 17 illustrates trapping of a cancer cell by an exemplary device.

FIG. 17 includes a photograph of a colon-rectal cancer cell (HT-29 cell line) isolated using the present subject matter. The flow direction in FIG. 17 is from right to left, and the biofluid consists of a dilute mixture of HT-29 cancer cells in McCoy's cell growth medium. The arrow in FIG. 17 marks the trapped cancer cell. Furthermore, additional devices or methods for cell separation (e.g. dielectrophoresis, electrophoresis, electrokinetic based separation, magnetically based separation, optically based cell sorting) or cell screening (e.g. fluorescence-based screening to identify cancer cells tagged with a dye-labeled antibody to cytokeratin from other cells) can be integrated downstream of this device to confirm the identity of the isolated cancerous cells.

Additional applications involving separation, concentration and isolation addressed by the present subject matter include fetal cell monitoring in maternal blood for prenatal diagnostic of genetic disorders and prion detection. A prion includes a small infectious proteinaceous particle which resists inactivation by procedures that modify nucleic acids. In addition, the present subject matter can be used with fetal cells (fetal cells are larger than maternal cells) and other micro-biological particulates or nano-biological particulates.

As used herein, filtration includes collecting the clarified filtrate as well as isolating and concentrating solids. Examples of filtering include partitioning biological cells and micro-particulates or nano-particulates. Examples of the present subject matter can be used for filtering, separating, isolating, concentrating and purifying.

In one example, the present subject matter includes a substrate material including, but not limited to, polymeric materials (polydimethylsiloxane (PDMS), polymethylmethacrylate (PMMA), polyethylene, polyester (PET), polytetrafluoroethylene (PTFE), polycarbonate, polyvinyl chloride, fluoroethylpropylene, lexan, polystyrene, cyclic olefin copolymers, polyurethane, polyestercarbonate, polypropylene, polybutylene, polyacrylate, polycaprolactone, polyketone, polyphthalamide, cellulose acetate, polyacrylonitrile, polysulfone, epoxy polymers, thermoplastics, fluoropolymer, and polyvinylidene fluoride, polyamide, polyimide), inorganic materials (glass, quartz, silicon, GaAs, silicon nitride), fused silica, ceramic, glass (organic), metals and/or other materials and combinations thereof.

In addition, the substrate can be fabricated of porous membranes, woven or non-woven fibers (such as cloth or mesh) of wool, metal (e.g. stainless steel or Monel), glass, paper, or synthetic (e.g. nylon, polypropylene, and various polyesters), sintered stainless steel and other metals, and porous inorganic materials such as alumna, silica or carbon.

The flow can be delivered by, for example, methods and devices that induce hydrodynamic fluidic pressure, which includes but is not limited to those that operate on the basis of mechanical principles (e.g. external syringe pumps, pneumatic membrane pumps, vibrating membrane pumps, vacuum devices, centrifugal forces, and capillary action); electrical or magnetic principles (e.g. electroosmotic flow, electrokinetic pumps piezoelectric/ultrasonic pumps, ferrofluidic plugs, electrohydrodynamic pumps, and magnetohydrodynamic pumps); thermodynamic principles (e.g. gas bubble generation/phase-change-induced volume expansion); surface-wetting principles (e.g. electrowetting, chemically, thermally, and radioactively induced surface-tension gradient).

In addition, fluid drive force can be provided by gravity feed, surface tension (like capillary action), electrostatic forces (electroosmotic flow), centrifugal flow (substrate disposed on a compact disc and rotated), magnetic forces (oscillating ions causes flow), magnetohydrodynamic forces and a vacuum or pressure differential.

Fluid flow control devices, such as those enumerated with regard to methods and devices for inducing hydrodynamic fluid pressure or fluid drive force, can be coupled to an input port or an output port of the present subject matter. In one example, multiple ports are provided at either or both of the inlet and outlet and one or more ports are coupled to a fluid flow control device.

The present subject matter can be fabricated by replication or direct fabrication. Examples include semiconductor fabrication techniques and methods including photolithography, growing a crystalline structure, and etching (reactive ion etching and wet etching), laser ablation, replica molding, injection molding and embossing (application of heat and pressure) and imprinting.

In various examples, the present subject matter is fabricated in the form of a membrane. The membrane can have a uniform thickness or a predetermined thickness gradient. In addition, the uniformity and numerosity of the pores can be tailored for a particular application. Furthermore, one or more particular coatings can be applied to an external or internal surface of the substrate. For example, the channel surfaces may be modified chemically to increase or decrease the surface interaction with the object or particulate to enhance device performance.

The present subject matter can be integrally fabricated on a chip or constructed off chip and then assembled onto a chip.

A micro-fabricated or nano-fabricated device and method of the present subject matter can be used to separate or filter microscopic or nanoscopic biological objects, such as biological cells, macromolecules, colloidal particles, particulates, or micro-beads.

A plurality of one-dimensional channels can be configured such that the longitudinal axis of each channel is aligned in parallel for axial flow. A radial configuration of longitudinal axis (converging at a point) yields a cross-flow filter. Other configurations are also contemplated, including, for example, a random arrangement of axes.

According to one example, an apparatus has one or more channels having an aperture cross sectional geometry such that a chord of length larger than the diameter of the object to be excluded can be drawn.

In particular, a channel having a convex cross sectional aperture, according to one example of the present subject matter, has an aperture width less than the width of the object to be excluded and the aperture diameter is greater than the diameter of the object and also greater than the aperture width.

In addition, a channel having a concave cross sectional aperture, according to one example of the present subject matter, has an inscribed convex polygon of a width and a diameter less than the width of the object to be excluded and a convex hull that has a diameter greater than the diameter of the object to be excluded.

In one example, the object is allowed to move in a direction parallel to the fluid flow. In other examples, the object is allowed to move in a direction at a particular angle relative to the fluid flow. That angle can be normal or at any other angle. For example, the object may be drawn by capillary action or diffusion in a direction that is not aligned with the fluid flow direction.

Cancer Metastases and CTCs.

Embodiments in accordance with the present invention relate to methods and apparatuses for concentrating and isolating CTCs from body fluids. One embodiment of the present invention includes a micro-fabricated or nano-fabricated device having channels configured for separating and excluding.

Embodiments in accordance with the present invention can be used to separate and enrich cancer cells from other cells that may be present in a body fluid. Some biological cells have cellular membranes that are not rigid and are thus highly sensitive to local pressure changes that are often present in the process of physical exclusion and separation. For example, in isolating cells by mechanical exclusion, exposure of the cells to a high-pressure environment can cause cell lysis.

To overcome these challenges in the separation and concentration of biological cells and particles, the present subject matter includes devices and methods for separating and concentrating biological cells or particles, while reducing the incidence of cell lysis during the separation, concentration, filtration or isolation procedure.

Embodiments in accordance with the present invention include channels having a particular cross-sectional shape for separating cancer cells from biofluids or immiscible objects from a fluid. The cross-sectional shape of the channels, as employed in embodiments of the present subject matter, reduce the hydrodynamic pressure experienced by the cells during the separation, isolation and concentration processes and therefore reduce the likelihood of cellular damage.

The present subject matter can be used as diagnostic in trapping rare circulating tumor cells (CTCs) in cancer monitoring.

Particular embodiments in accordance with the present invention relate generally to methods and systems to isolate or enrich tumor cells in biofluids for the diagnosis of cancer, and in particular but not by way of limitation, to methods and systems that reduce cell lysis or cellular membrane damage during the isolation or enrichment of tumor cells.

The spreading of cancer cells from the primary tumor is an important factor governing the probability of relapse and the survival rate in cancer patients. Often it has been argued that metastases rather than the primary tumors are responsible for most tumor deaths. Clinically the rate of metastases is quite high: about 50% of breast cancer cases that were thought to be localized can become metastatic, and even 30% of patients with node-negative diagnosis can be expected to develop distant metastases within five years.

Since cancer cells have the ability to stimulate angiogenesis, as the cells grow unregulated and lose their ability to adhere to each other, they can enter the blood and lymphatic circulation and circulate throughout the body. These cells are often referred to as Circulating Tumor Cells (CTC), Disseminated Tumor Cells (DTC), Circulating Cancer Cells (CCC), Circulating Epithelial Cells (CEC), Occult Tumor Cells (OTC), or other similar permutations to indicate the mobile nature of these cells, in contrast to the specimens obtained by direct biopsy of solid tumors. CTCs have been detected in the blood of patients suffering from all major cancers: prostate, ovarian, breast, gastric, colorectal, renal, lung, pancreatic, and others.

The cancer metastasis mechanism involves multiple processes: first, after the tumor cells are shed from the primary tumor, they follow the circulation pattern and become arrested at various organs and capillaries. Once arrested, tumor cells have certain probability of developing into tumors, depending on the local chemical environments, or molecular regulations, which may foster CTC accumulation and encourage the growth of blood vessels to sustain the new tumors.

The physical circulation pattern describes the trajectory of the CTCs and partially explains why, depending on the location of the primary tumor, there are organ-specific patterns in the metastases process. For example, CTCs from a breast tumor may follow the blood circulation, which would first travel through heart, then the capillaries of the lungs, and then taken to all other organs via the systemic arterial circulation.

Clinically it has been observed that breast cancer metastases can occur in bone, liver, brain and lungs. On the other hand, CTCs from a colon tumor would be taken first to the capillaries of the liver, through the heart, the capillaries of the lungs, and then the arterial circulation.

This circulation pattern explains well why clinically colorectal cancers tend to spread to liver initially. During the circulation process, CTCs are lodged at various locations because of size restriction: while typical capillaries range between 3-8 µm in diameter, CTCs can be as large as 20 µm or more. Capillaries in the lungs and the livers are thus particularly vulnerable to the lodging of CTCs.

In addition to the physical circulation mechanism, some researchers have argued that chemical "homing" signals such as chemokines and their receptors may preferentially attract CTCs to specific organs. For example, chemokine receptors CXCR4 and CCR7 are expressed in breast cancer CTCs, while lymph nodes, lung, liver, and bone marrow are known to be rich in the corresponding ligands CXCL12 and CCL21.

Once CTCs become lodged, their ability to grow into a sustaining tumor depends on local chemical environment. Presence of growth factors such as parathyroid hormone-related protein and transforming growth factor-$\beta$ (TGF-$\beta$) in the bones, for example, can stimulate growth.

CTC Screening.

CTCs in blood can be used as an additional prognostic factor for the cancer patients. The strength of a CTC test is in its ability to measure how cancer cells disseminate, before they become tumors large enough to be detectable by imaging methods. The most important benefit—that of saving life—is its role in determining whether a treatment is effective. A cancer patient can also expect significant cost-saving if a CTC test can eliminate unnecessary (and often not covered by insurance) Computed Tomography (CT) or Positron Emission Tomography (PET) scans, or shorten the drug treatments that are ineffective.

CTC test is designed to count the number of tumor cells present in a blood sample and allow a pathologist to visually examine the cells. Careful examination of cytomorphology can yield the origin of CTCs and the developmental stage of cancer. Select clinical literature has reported that cancer patients with as little as 5 CTCs in their blood sample have a much lower survival rate. However, forecasting doom is not the point of a CTC test. It is about learning the result early, interpreting it as a warning sign that the current treatment is not effective, and promptly switch to a more aggressive treatment strategy before it is too late.

CTCs are very different from the ordinary blood cells, which include the red blood cells, the white blood cells, and platelets. Platelets are on only about 2-4 µm in diameter, which is much smaller than other blood cells. Red blood cells are highly flexible fluidic sacs delivering nutrients and oxygen to various parts of the body. A red blood cell has no internal compartments (organelles) inside and carries no DNA. A healthy red blood cell looks like a doughnut ("biconcave") with a diameter of ~7 µm. White blood cells have internal compartments (organelles), which render them more rigid than red blood cells. Ranging between 7-20 µm in diameter, white blood cells exists in several varieties, performing different immunity-related functions. On the other hand, CTCs are substantially larger than these blood cells. CTCs also have internal compartments (organelles) that contain DNAs—especially the DNA of the tumor source that the CTCs came from. CTCs may also carry an abundance of abnormal proteins found in the tumor source.

Accurate isolation and detection of CTCs is not a trivial task. CTCs are present in extremely low concentration in the peripheral blood, estimated to be on the order of one tumor cell per 10E6 to 10E7 mononuclear cells, which is equivalent to one tumor cell per 0.5 ml to 5 ml of peripheral blood. At such low concentration, a sample with estimated 100 million cells must be screened in order to detect at least one CTC with 99.995% certainty. An automatic digital microscopy (ADM) scanning at a typical speed of 800 cells/second would require 18 hours to complete a sample that size, and even with an improved optical system, it is estimated that the scanning task would still require about one hour with additional manual examination.

Biological cells are often sensitive to local pressure change because cellular membranes are not rigid. In filtering or isolating cells by mechanical exclusion, exposure of the cells to a high pressure environment can cause lysing. Lysis refers to the disintegration, rupturing or destruction of a cell. With a cell, such a breakdown is caused by damage to the plasma (outer) membrane and subsequent loss of cell contents (cytoplasm, organelles or nucleus) resulting from physical insult to the cell. The present subject matter reduces the incidence of lysis in separation, concentration, filtration or isolation.

According to an embodiment of the present invention, a biofluid sample may be injected into the device described in the present invention, which contains an array of one-dimensional channels to exclude the CTCs. As the biofluid moves through the device, the concentration of CTC is increased (enriched) as undesirable components of blood, such as platelets, red blood cells, and white blood cells, preferentially exit the one-dimensional channels. The exit side of the one-dimensional channels may be interconnected to larger flow channels to facilitate the removal of the undesirable components. A collection area for CTCs may be constructed by surrounding an open area with one-dimensional channels.

In accordance with one embodiment of the present invention, one or more walls forming the one-dimensional channels may be made from optically transparent material, such that an exemplary device may be placed under a microscope for inspection and viewed through such walls.

In accordance with certain embodiments, prior to the injection the biofluid may be diluted.

In accordance with certain embodiments, prior to the injection the biofluid may be stabilized using a fixative to preserve the integrity of cellular membranes and prolong the shelf-life.

Prior to the injection the biofluid may be treated with cell-permeating dyes, antibodies attached with fluorescent molecules, or other fluorescent entities (e.g. quantum dots, nanoparticles, nanobeads, nanocages, or photoactivated fluorophores), fluorescent probes against cell surface molecules or entities, fluorescent probes against intracellular molecules or entities, aptamers, or any other fluorescent compounds, to aid visualization. Alternatively the biofluid may be treated with fluorescent, magnetic, electroactive, or photoactive agents that bind preferentially to a specific population or subpopulation of cells. In a specific example, the agent binding to the target may be an antibody. In accordance with certain embodiments, this pre-collection treatment can aid in the identification of particular targets, for example subpopulation of cancer cells such as putative cancer stem cells.

Further alternatively, following collection of the entities of interest from the biofluid, the device may be treated with cell-permeating dyes, antibodies, aptamers, compounds that bind to cell surface molecules or intracellular molecules of interest, as well as fluorescent, magnetic, electroactive, bioactive or photoactive agents that bind preferentially to a collected entity of interest. This post-collection treatment can aid in the identification of particular targets, for example subpopulation of cancer cells such as putative cancer stem cells.

The channel surfaces may be treated with anticoagulant compounds, compounds that preferentially bind to CTCs, or compounds that prevent sticking of cells.

After the injection of CTC-containing biofluids additional dyes or dye-conjugated molecules (such as antibodies, fab fragments, aptamers, ligands, agonists, antagonists, or combinations thereof) may be introduced into the device to accentuate cellular features and assist the identification of tumor cells. An example is to use a stain that reacts with cytokeratins, which are integral components of the cytoskeleton in epithelial cells, to indicate that the cells come from epithelial sources (most tumors occur in epithelial tissues) rather than blood sources.

Other dye examples include flurorescein isothiocyanate (FITC)-conjugated mouse anti-human epithelial antibody (HEA) and phycoerythrin (PE)-conjugated anti-CD45. Other examples of dye-conjugated antibodies include but are not limited to the pan-cytokeratin antibody A45B/B3, AE1/AE3, or CAM5.2 (pan-cytokeratin antibodies that recognize Cytokeratin 8 (CK8), Cytokeratin 18 (CK18), or Cytokeratin 19 (CK19) and ones against: breast cancer antigen NY-BR-1 (also known as B726P, ANKRD30A, Ankyrin repeat domain 30A); B305D isoform A or C (B305D-A or B305D-C; also known as antigen B305D); Hermes antigen (also known as Antigen CD44, PGP1); E-cadherin (also known as Uvomorulin, Cadherin-1, CDH1); Carcino-embryonic antigen (CEA; also known as CEACAM5 or Carcino-embryonic antigen-related cell adhesion molecule 5); β-Human chorionic gonadotophin (β-HCG; also known as CGB, Chronic gonadotrophin, β polypeptide); Cathepsin-D (also known as CTSD); Neuropeptide Y receptor Y3 (also known as NPY3R; Lipopolysaccharide-associated protein3, LAP3, Fusion; Chemokine (CXC motif, receptor 4); CXCR4); Oncogene ERBB1 (also known as c-erbB-1, Epidermal growth factor receptor, EGFR); Her-2 Neu (also known as c-erbB-2 or ERBB2); GABA receptor A, pi (π) polypeptide (also known as GABARAP, GABA-A receptor, pi (π) polypeptide (GABA A(π), γ-Aminobutyric acid type A receptor pi (π) subunit), or GABRP); ppGalNac-T(6) (also known as β-1-4-N-acetyl-galactosaminyl-transferase 6, GalNActransferase 6, GalNAcT6, UDP-N-acetyl-d-galactosamine:polypeptide N-acetylgalactosaminyltransferase 6, or GALNT6); CK7 (also known as Cytokeratin 7, Sarcolectin, SCL, Keratin 7, or KRT7); CK8 (also known as Cytokeratin 8, Keratin 8, or KRT8); CK18 (also known as Cytokeratin 18, Keratin 18, or KRT18); CK19 (also known as Cytokeratin 19, Keratin 19, or KRT19); CK20 (also known as Cytokeratin 20, Keratin 20, or KRT20); Mage (also known as Melanoma antigen family A subtypes or MAGE-A subtypes); Mage3 (also known as Melanoma antigen family A 3, or MAGA3); Hepatocyte growth factor receptor (also known as HGFR, Renal cell carninoma papillary 2, RCCP2, Protooncogene met, or MET); Mucin-1 (also known as MUC1, Carcinoma Antigen 15.3, (CA15.3), Carcinoma Antigen 27.29 (CA 27.29); CD227 antigen, Episialin, Epithelial Membrane Antigen (EMA), Polymorphic Epithelial Mucin (PEM), Peanut-reactive urinary mucin (PUM), Tumor-associated glycoprotein 12 (TAG12)); Gross Cystic Disease Fluid Protein (also known as GCDFP-15, Prolactin-induced protein, PIP); Urokinase receptor (also known as uPR, CD87 antigen, Plasminogen activator receptor urokinase-type, PLAUR); PTHrP (parathyrold hormone-related proteins; also known as PTHLH); BS106 (also known as B511S, small breast epithelial mucin, or SBEM); Prostatein-like Lipophilin B (LPB, LPHB; also known as Antigen BU101, Secretoglobin family 1D member 2, SCGB1D2); Mammaglobin 2 (MGB2; also known as Mammaglobin B, MGBB, Lacryglobin (LGB) Lipophilin C (LPC, LPHC), Secretoglobin family 2A member 1, or SCGB2A1); Mammaglobin (MGB; also known as Mammaglobin 1, MGB1, Mammaglobin A, MGBA, Secretoglobin family 2A member 2, or SCGB2A2); Mammary serine protease inhibitor (Maspin, also known as Serine (or cystein) proteinase inhibitor clade B (ovalbumin) member 5, or SERPINB5); Prostate epithelium-specific Ets transcription factor (PDEF; also known as Sterile alpha motif pointed domain-containing ets transcription factor, or SPDEF); Tumor-associated calcium signal transducer 1 (also known as Colorectal carcinoma antigen CO17-1A, Epithelial Glycoprotein 2 (EGP2), Epithelial glycoprotein 40 kDa (EGP40), Epithelial Cell Adhesion Molecule (EpCAM), Epithelial-specific antigen (ESA), Gastrointestinal tumor-associated antigen 733-2 (GA733-2), KS1/4 antigen, Membrane component of chromosome 4 surface marker 1 (M4S1), MK-1 antigen, MIC18 antigen, TROP-1 antigen, or TACSTD1); Telomerase reverse transcriptase (also known as Telomerase catalytic subunit, or TERT); Trefoil Factor 1 (also known as Breast Cancer Estrogen-Inducible Sequence, BCEI, Gastrointestinal Trefoil Protein, GTF, pS2 protein, or TFF1); or Trefoil Factor 3 (also known as Intestinal Trefoil Factor, ITF, p1.B; or TFF3).

After the injection of biofluids, additional reagents may be introduced to analyze the cellular contents (DNA or proteins encapsulated by the CTCs) to determine the molecular origins of cancer.

The device according to embodiments of the present invention may incorporate additional resistive heating elements to perform on-chip cellular assays such as Polymerase Chain Reaction (PCR) or Time Polymerase Chain Reaction (RT-PCR).

The device according to embodiments of the present invention may incorporate electrodes to manipulate the trajectory of select cells or biofluid to enhance the separation base on phenomena such dielectrophoresis or electrowetting.

The device according to embodiments of the present invention may include magnetic elements to manipulate the trajectory of select cells to improve separation base on the magnetic susceptibility of the cells or the micro-magnetic or nano-magnetic particles attached to the cells.

The device according to embodiments of the present invention may include electrodes to conduct on-chip chemical assay such as electrophoresis or electrochromatography.

Electric field or magnetic field may be applied to force a subpopulation of cells to deviate from normal flow pattern and enhance the separation of cells.

Figure 18:
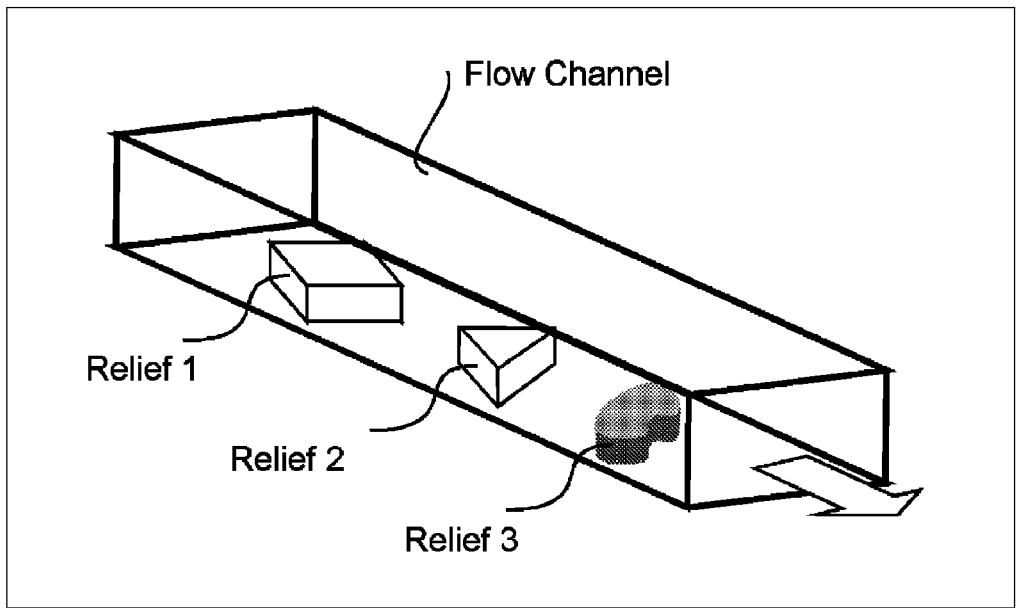
FIG. 18 illustrates a flow channel with examples of relief patterns (topographical features) on the bottom wall of the channel.

Topographical features or relief patterns may be incorporated into the walls of channels to create pressure gradients which favor concentrating or dispersing of select cells. FIG. 18 illustrates how such relief patterns may be incorporated. FIG. 18 illustrates a flow channel with examples of relief patterns (topographical features) on the bottom wall of the channel. Arrow indicates the direction of flow. Relief 1 shows a diamond-shaped relief at the bottom of the flow channel. Relief 2 shows a triangular shaped relief at the bottom of the flow channel. The reliefs may span any or combinations of the four walls that form the flow channel. Multiple reliefs or combinations of different shapes of reliefs may be used. The shapes of the reliefs can be any arbitrary shape, shown as in Relief 3.

Figure 19:
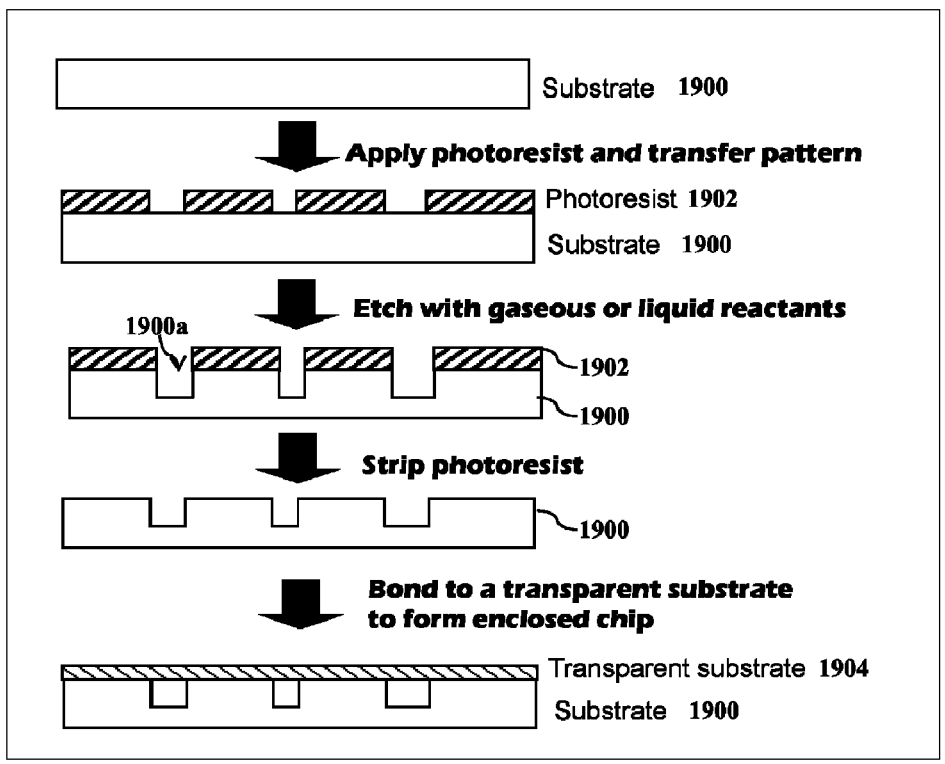
FIG. 19 illustrates a production process of an exemplary device using direct etching.

Devices in accordance with embodiments of the present invention may be fabricated using a variety of methods. FIG. 19 shows a lithographic technique to directly fabricate features on such a chip using direct etching. In a first step a substrate 1900 is provided. In the next step photoresist 1092 is applied to the surface of the substrate and then developed to transfer a pattern. Next, portions 1900a of the substrate 1900 exposed by the patterned photoresist, are subjected to etching with gaseous or liquid reactants. The photoresist pattern is then removed, and a transparent substrate 1904 is bonded to the substrate to form an enclosed chip.

Figure 20:
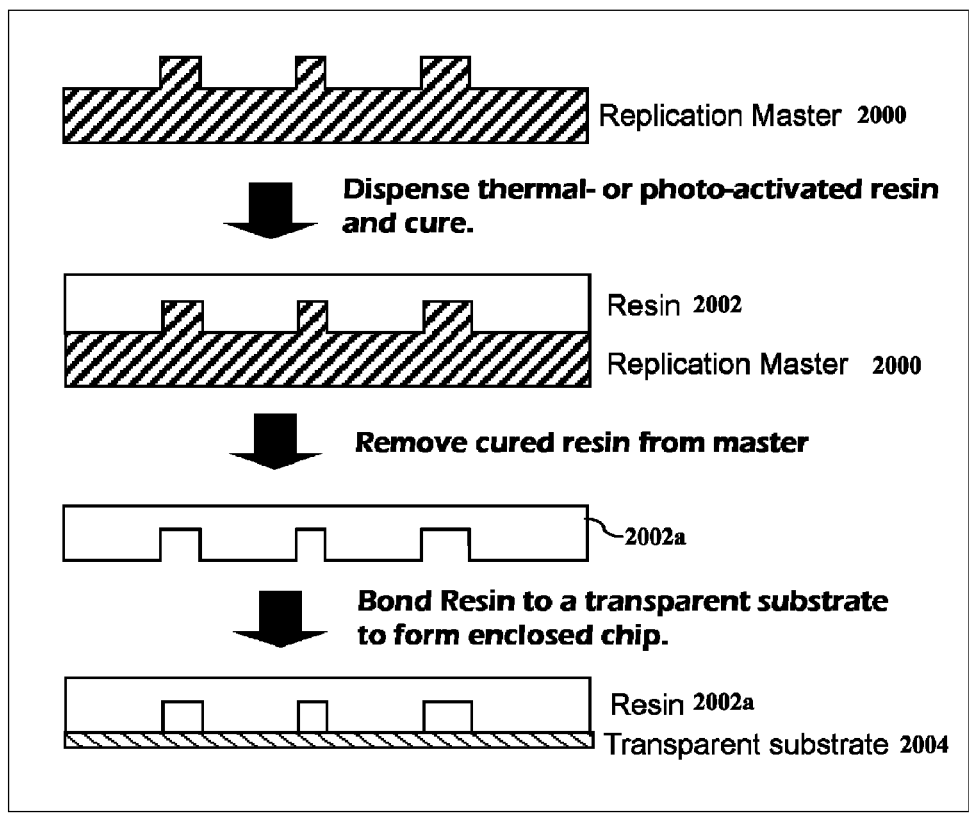
FIG. 20 illustrates a production process of an exemplary device using polymer resin to replicate from a master mold.

Alternatively, FIG. 20 illustrates a production process of an exemplary device using polymer resin to replicate from a master mold. First, a replication master 2000 exhibiting a surface relief pattern is formed. Next, resin 2002 is applied over the replication master and then cured. In the next step, the cured resin 2002a is removed from the master. Finally, the cured resin is bonded to a transparent substrate 2004 to form the enclosed chip.

The device may include flow channels having a dimension that is specifically limited in size in order to capture and collect cancer cells, while allowing fluid to flow around the captured cell. Examples of such 1D flow channels include but are not limited to those having a maximum single dimension of 5 µm, 10 µm, 15 µm, 20 µm, 25 µm, 30 µm, 35 µm, 40 µm, 45 µm, or 50 µm.

Effusive Filtration

One technique which may particular effective in isolating CTC's without damage is effusive filtration. For purposes of this application, "effusive filtration" refers to configurations where the flowing fluid is actively dispersed or redistributed by the filtration media and/or morphological features inside the flow channel, such that the local fluid velocity across the filtration media is tuned to minimize the degree of physical impact of biological cells during the exclusion process. The flow may be dispersed in two-dimensions or three-dimensions to reduce the fluid velocity in the direction of direct impingement of the filtration medium.

FIG. 29 shows a simplified plan view of an example of effusive filtration in accordance with an embodiment of the present invention. Specifically, FIGS. 29A-B show an example of effusive filtration, where the filtration medium is an array of 1-D channels, positioned such that they converge toward the center of the main flow. FIG. 29A is an illustration and FIG. 29B is a photograph of the streamlines mapped using fluorescent nanoparticles.

Flow Line A of FIG. 29A illustrates the trajectory of a fluid element closer to the conduit wall, traveling to the right, but is forced through a 1-D channel when obstructed by the walls of 1-D channels at an angle, to join the permeate side of the filter. Flow Line B of FIG. 29A illustrates the trajectory of a fluid element closer to the center of the main flow, traveling essentially in parallel to the walls of the 1-D channels.

Flow Line C (dashed line) of FIG. 29A illustrates that where the feed channel is constricted as a result of the convergence, fluid on the permeate side may overflow back across the filtration medium downstream from where the fluid element initially crossed to join the feed side. The condition for backflow depends on the magnitude of the feed velocity, the relative fluidic resistances locally across the 1-D channels as well as the resistances of the flow conduits on the retentate side and the permeate side.

Figure 30B:
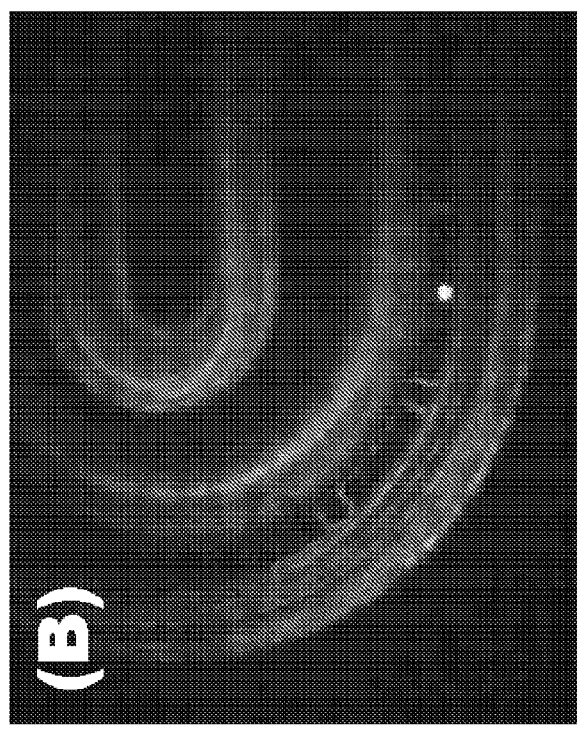
FIGS. 30A-B show an example of effusive filtration featuring a 180-degree bend.
Figure 30A:
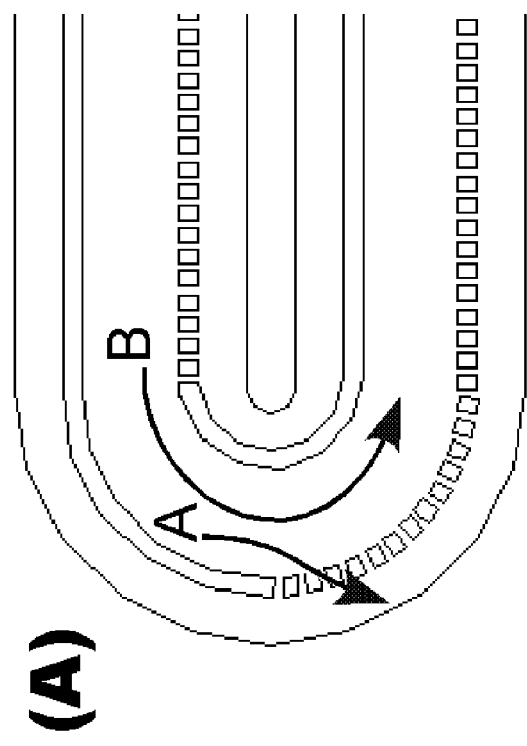

FIGS. 30A-B illustrate an alternative embodiment of an apparatus configured to perform effusive filtration. This embodiment uses effusive filtration in the form of a bend or curve in the channel to disperse the flow. FIG. 30A is an illustration and FIG. 30B is a photograph of the streamlines mapped using fluorescent nanoparticles.

Flow Lines A and B illustrate the trajectories of fluid elements in a 180° bend, where a portion of the outer wall of the bend is a filtration medium consisting of an array of 1-D channels. Flow Line A illustrates that, because the walls of 1-D channels does not provide sufficient centripetal force to keep the fluid element in a circular trajectory, the fluid element traverses through the 1-D channels and join the permeate side. Flow Line B illustrates that fluid elements closer to the inner side of the bend can follow a path parallel to the bend. The ratio of permeate to retentate (flows across the filtration medium and that remaining the main flow conduit) is highly dependent of the feed velocity.

In this example of effusive filtration, increasing the feed velocity can result in an improvement in separation. Increasing the feed velocity results in higher centrifugal force experienced by objects traveling through the bend, thus objects of different sizes or densities may be preferentially separated. In addition, centrifugal force also results in forcing more portion of the feed through 1-D channels, thus increasing the permeate and improving the separation.

The placement of 1-D channels need not be regularly spaced. 1-D channels may be separated by a large distance (a long wall) which may be used to alter the directions of the fluid. For example, the upstream outer boundary of the bend provided necessary centripetal force to keep the fluid traveling through an arc.

FIG. 31 illustrates another embodiment of a structure for performing effusive filtration. In this embodiment, the feed is dispersed to distribute the fluid velocity to improve filtration. FIG. 31A is an illustration and FIG. 31B is a photograph of the streamlines mapped using fluorescent nanoparticles.

Because the flow conduit features an expansion upstream, the fluid velocity now contains two components: horizontal (along the direction of inlet feed) and vertical (along the direction of expansion). Flow Line A illustrates a flow trajectory where it is largely horizontal. Flow Lines C and D illustrate trajectories that have comparable horizontal and vertical components.

Flow Line B (dashed line) illustrates a flow trajectory that is largely parallel to the expanding wall, and results in a flow largely tangential to the 1-D channels. Flow line B replaces Flow Line D when the fluidic resistance of the filtration medium ordinarily crossed by Flow Line D is larger than the fluidic resistance of the filtration media crossed by Flow Line A or C. This configuration may arise if the filter section crossed by Flow Line D has 10 nm-wide 1-D channels whereas the sections crossed by Lines A and C have 20-um-wide 1-D channels; or if the filter section crossed by Flow Line D is blocked by cells such that the fluidic resistance increases dynamically.

In the above embodiment, certain apertures are oriented in a direction substantially perpendicular to the direction of flow in order to accomplish axial filtration of the entity. Examples of such apertures are those located at the far end of the chamber of FIG. 31A, through which flow line A passes. Other apertures in this embodiment are oriented in a direction not substantially perpendicular to the direction of flow in order to accomplish cross-flow filtration of the entity, for example the apertures in the example of FIG. 30A.

Thus, in a closed filtration system it is possible to exhibit characteristics of tangential flow (Flow Line B), as well as axial flow (Flow Line A). However, because of the flow dispersing and the positioning of the 1-D channels, the fluid velocity impinging on the 1-D channels is decreased significantly as compared with the inlet feed velocity. This lessening of impinging fluid velocity reduces the physical impact against the walls of the 1D channels, reducing the likelihood of membrane damage and even cell lysis, thereby offering a possible advantage over conventional techniques.

Additional details regarding the nature and application of effusive filtration are described in U.S. nonprovisional patent application Ser. No. 11/766,053 filed Jun. 20, 2007 and incorporated by reference herein for all purposes.

EXAMPLES

Example 1

Breast Cancer

Figure 21B:
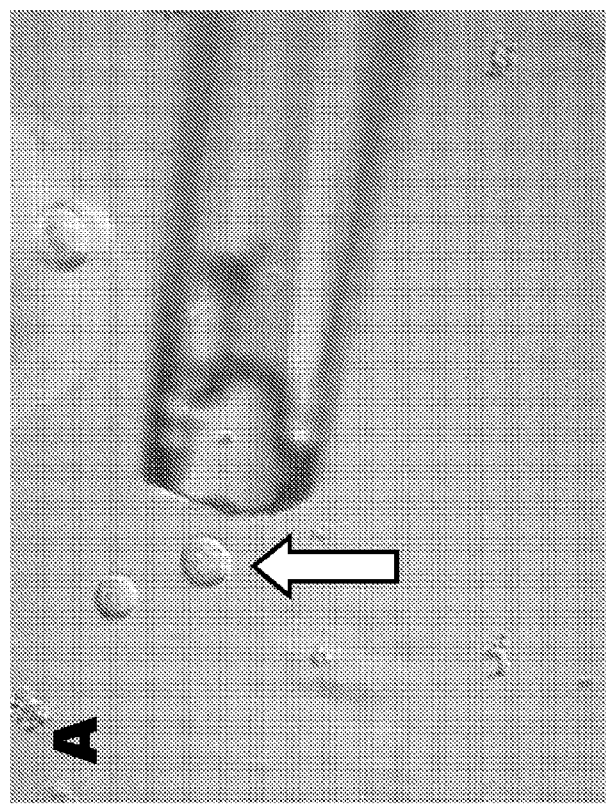
FIGS. 21A and 21B illustrate the preparation of tumor cell samples by using a micropipette to pick up individual tumor cells (arrow).
Figure 21A:
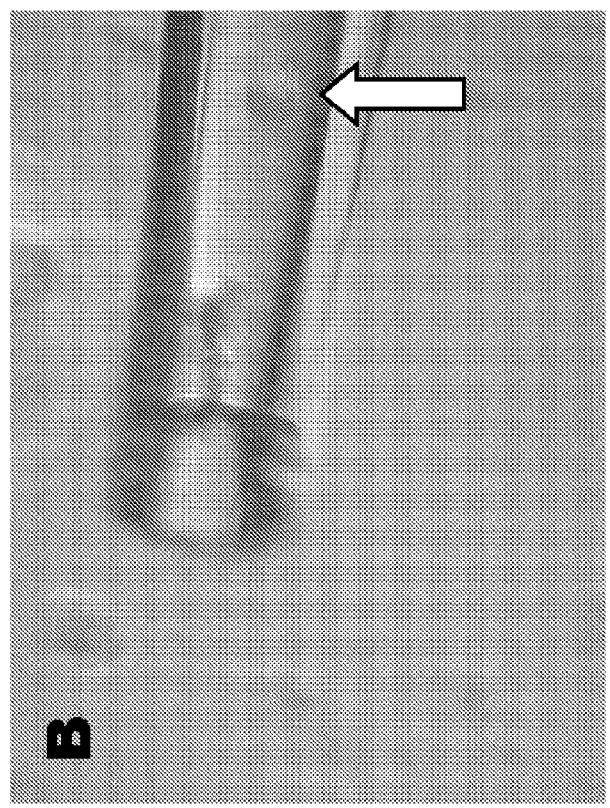

Breast cancer cells (MCF-7, human breast cancer) were cultured in Minimal Essential Media (MEM) with Earl's balanced salt solution supplemented with 10% fetal bovine serum and 1% antibiotics (penicillin/streptomycin). Loose tumor cells (10-50 cells) were extracted from the culture solution using a micropipette (FIGS. 21A-21B). The extracted cells were fixed using a formalin solution (5-40% in final volume) for 30 minutes. The nominal diameter of MCF-7 cells was 25 μm.

Exemplary devices were fabricated using the approach shown in FIG. 19. The 1-D channels were configured to line the perimeters of a long serpentine channel, with features to disperse the fluid and reduce the velocity of the flow component directly impinging upon the walls of the 1-D channels. The features that affected the impinging velocity included the relative flow resistances of the serpentine channel and the permeate channels (e.g. length, width, bending, corners), and the local flow resistance through 1-D channels (e.g. length, width, angle with respect to flow). The exemplary device was optimized to handle an overall fluidic throughput of 0.01-10 mL/min, while maintaining the impinging velocity below 3 cm/sec. This impinging velocity represents a 500-fold reduction as compared with the impinging velocity of an axial-flow filter of identical channel cross-section (10,000 μm$^2$). Specifically, use of a conventional axial-flow filter of comparable channel cross-section instead of the instant effusive filtration device, would produce an impinging velocity of ~1500 cm/sec, resulting in the lysis of filtered cells.

The fixed tumor cells were injected into an exemplary device using a 1 mL syringe, 20 G1½ needle, PE100 tubing, and a syringe pump. Tumor cells were counted as they entered the active region of an exemplary device ("cells into system"). Tumor cells trapped by the one-dimensional channels were subsequently counted ("cells trapped") and a ratio of cells trapped versus cells introduced into an exemplary device was computed for according to Eq. (8) below.

The results of the recovery testing are shown in FIG. 22A, with breast cancer data indicated in ♦. FIG. 22A illustrates an average recovery 92% of all breast cancer cells introduced into the device. FIG. 22B shows an image of a breast cancer cell (arrow) traveling through an exemplary device.

% Recovery=[(cells trapped)/(cells into system)]×100    Eq. (8)

To demonstrate the separation of tumor cells from blood cells, a known quantity of breast cancer cells (MCF-7) were first labeled with DiI lipophilic membrane fluorescent stain and then mixed with 1 mL of 1:10 solution of normal whole human blood and 1× phosphate buffer solution (PBS), again using a micropipette as illustrated in FIGS. 21A-B. The whole blood was also fixed with 5-40% formalin for 30 minutes. The mixture was then injected into an exemplary device to determine the recovery rate of breast cancer cells at a flow rate between 0.01-5 mL/min.

Figures 23A, 23B, 23C:
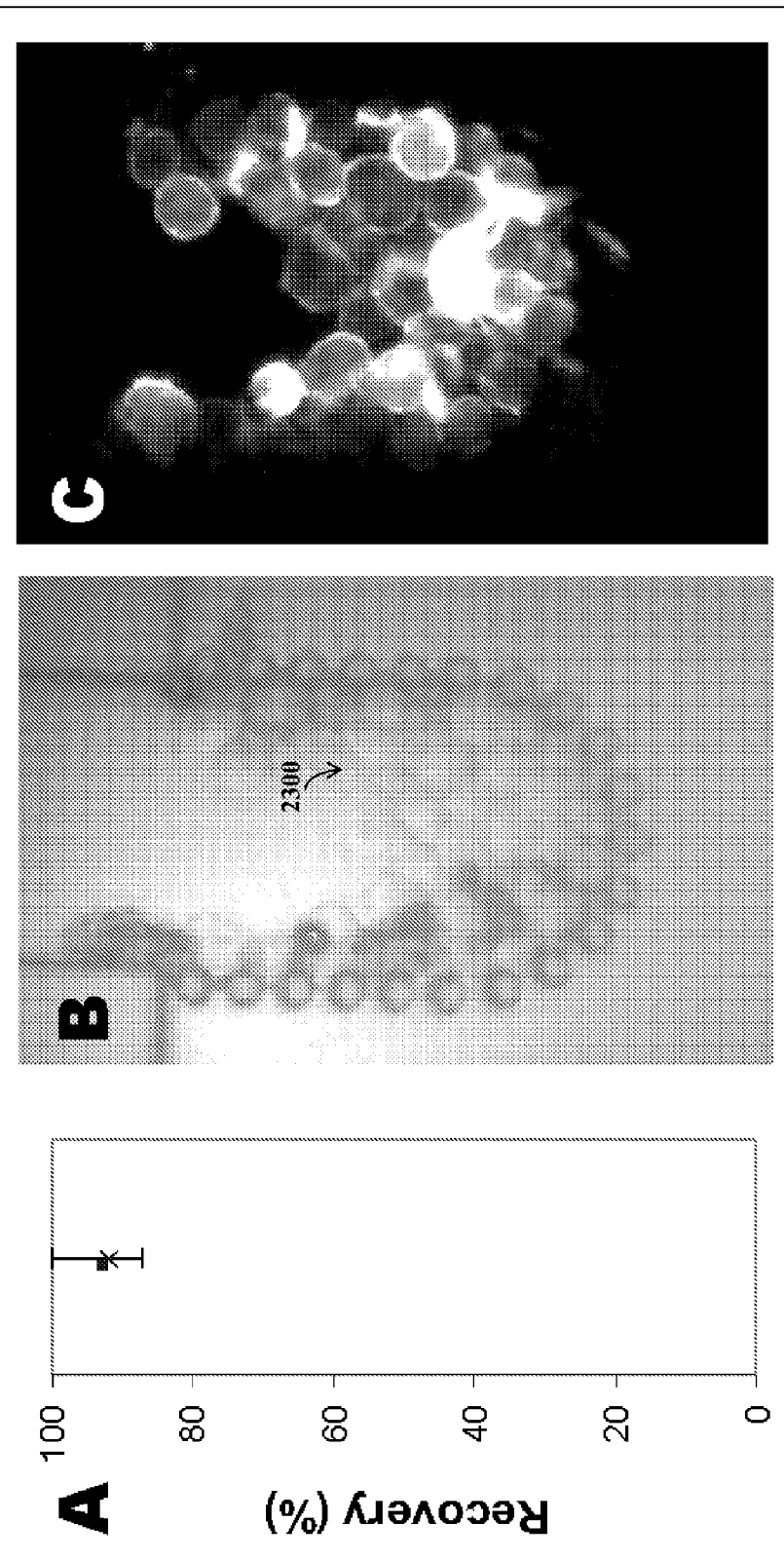
FIG. 23A illustrates the percent of breast cancer cells recovered using an exemplary device in a sample mixed with human whole blood.
FIG. 23B illustrates the breast cancer cells isolated using an exemplary device.
FIG. 23C illustrates the fluorescent image of FIG. 23B to confirm that the cells isolated were indeed cancer cells.

FIG. 23A shows a median recovery of 92% of the tumor cells and the statistical spread from multiple runs. FIG. 23B is a bright field photograph of cancer cells trapped in the collection region of an exemplary device, where approximately 20 breast cancer cells were trapped. FIG. 23C shows a fluorescent image of the same area, indicating that the cells collected were indeed the breast cancer cells previously labeled with DiI.

Example 2

Lung Cancer

Lung cancer cells (A549, human non-small cell lung cancer) were cultured in Dulbecco's Modified Eagles Medium (DMEM) with 4.5 g/L glucose, L-glutamine, and Sodium Pyruvate, 10% fetal bovine serum, 1% MEM amino acids, 1% Glutamax, and 1% antibiotics (penicillin/streptomycin). They were fixed with 5-40% formalin (final volume) for 30 minutes before injection into an exemplary device.

Microfluidic devices having the same architecture and formed in the same manner as those described in Example 1 above, were used. The injection protocol was identical to that described in Example 1. The nominal diameter of A549 cells was 20 μm.

Figure 24:
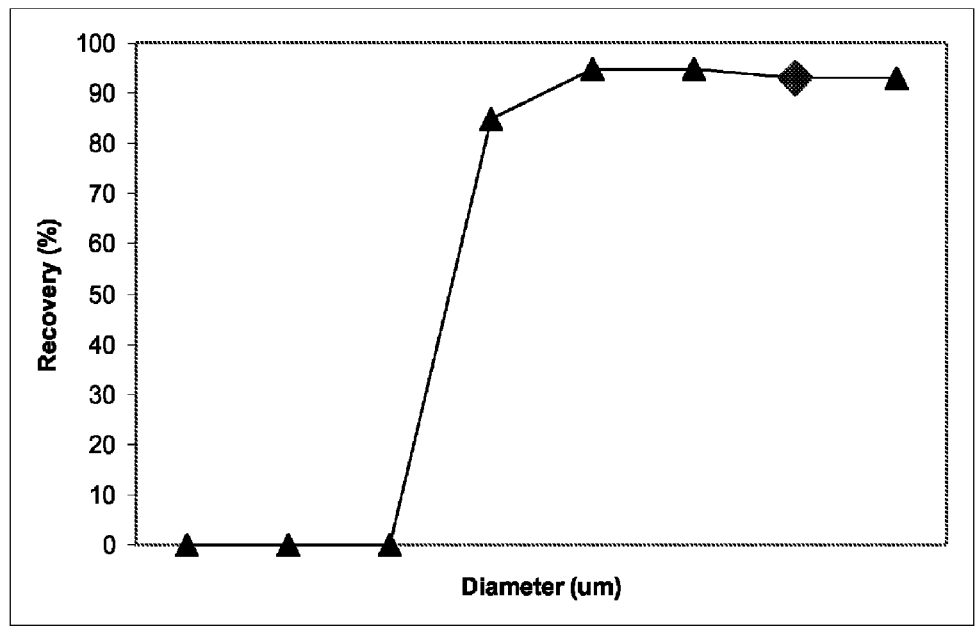
FIG. 24 illustrates the percent of lung cancer cells (A549, indicated with ♦) recovered using an exemplary device.

More than 90% of lung cancer cells were recovered as shown in FIG. 24 (indicated with ♦) using an exemplary device, under a volumetric flow rate between 0.01-5 mL/min.

Example 3

Colorectal Cancer

Colorectal cancer cells (HT-29, human colorectal cancer) were cultured in McCoy's 5A Modified Medium with 1.5 mM L-glutamine, 2200 mg Sodium Bicarbonate/L, 10% fetal bovine serum, and 1% antibiotics (penicillin/streptomycin). They were fixed with 5-40% formalin (final volume) for 30 minutes before injection into an exemplary device. The nominal diameter of HT-29 cells was 16 μm.

Figure 25:
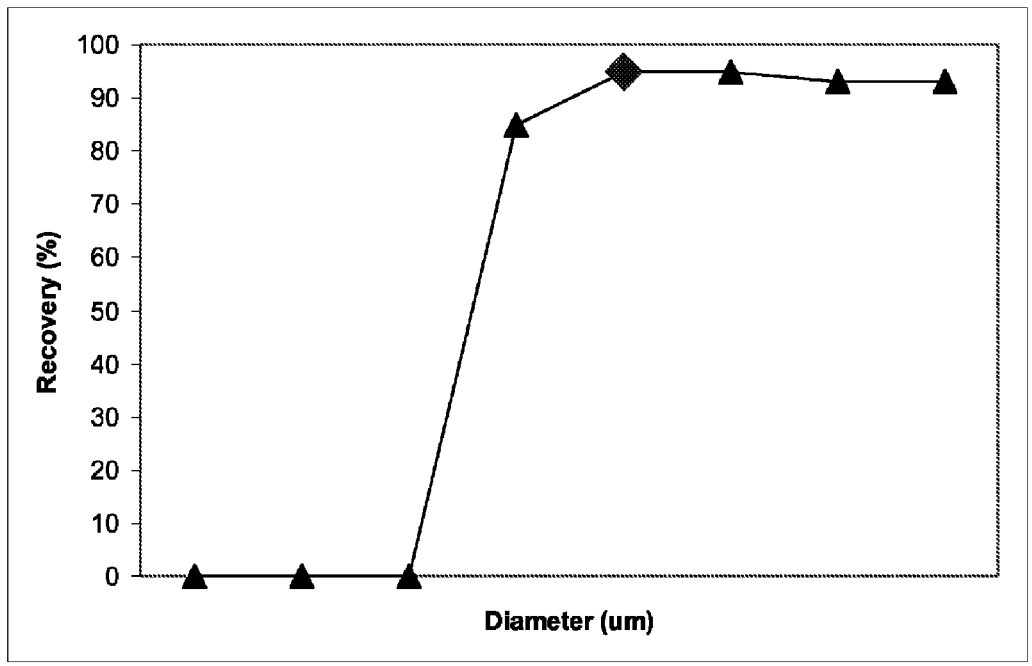
FIG. 25 illustrates the percent of colorectal cancer cells (HT-29, indicated with ♦) recovered using an exemplary device.

Also more than 90% of colorectal cancer cells were recovered as shown in FIG. 25 (indicated with ♦) using an exemplary device, under a volumetric flow rate between 0.01-5 mL/min.

Example 4

Figure 26:
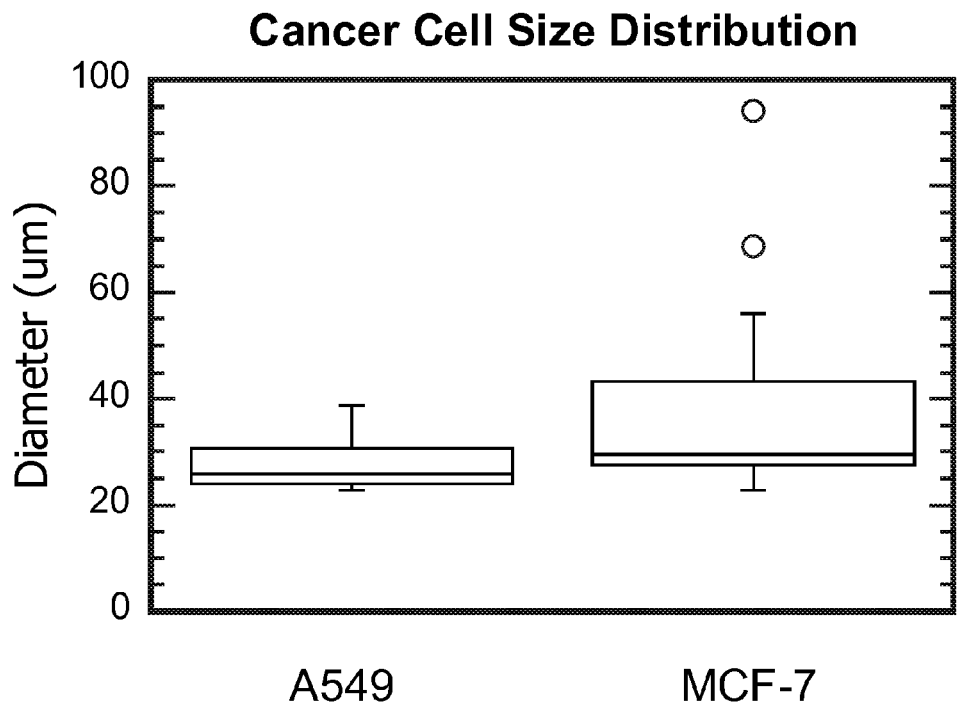
FIG. 26 shows a size distribution of cancer cells from lung (A549) and breast (MCF-7) cell lines.

The size distributions of several cultured cancer cell lines were measured using an image analysis software. The distributions of the cell diameter are shown in the statistical box plot (FIG. 26): A549 (non-small cell lung cancer) and MCF-7 (breast cancer). Both non-small cell lung cancer and breast cancer cells are mostly between 20-40 microns. Table 1 below lists additional measurements of cancer cells compiled from various literature sources, again showing cell diameters larger than 25 um in general.

TABLE 1

Cancer cell size measurements compiled from scientific literature.

| Cancer Cells | Average Diameter (um) |
|---|---|
| Cervical Cancer (HeLa) | 28 |
| Liver Cancer (HepG2) | 28 |
| Liver Cancer (He3B) | 32 |
| Prostate Cancer (LNCaP) | 27 |

Because red blood cells, which constitute 99.9% of cells in blood, are on the order of 7 microns, simple size exclusion principle can easily accomplish 1,000 fold enrichment. For non-small cell lung cancer and breast cancer, because these cells are significantly larger than even most white blood cells, simple size exclusion principle alone can provide an extremely high degree of enrichment (easily 100,000 fold enrichment).

In this example, cancer cells were labeled with 1 uM lipophilic dye DiI (Ex: 550 nm, Em: 570 nm) prior to spiking into blood sample. Accurately known cultured MCF-7 cells were spiked into 1 mL of whole human blood using a microcapillary mounted on a micromanipulator. The number of breast cancer cells ranged between 0-60. The blood sample was then diluted with phosphate buffered saline solution to produce 1:1 solution of whole blood to 1×PBS. The blood sample was then transferred into a syringe with the outlet connected to the chip using a PE 100 tubing, and the syringe was mounted onto a syringe pump, operating between 0.01 mL/min and 0.5 mL/min. After the injection into the chip was complete, the chip was inspected under a Nikon (TE2000) microscope under 20× magnification to identify the cancer cells isolated. Fluorescent identification was accomplished using a green laser (Em 532 nm) at approximately 5 mW.

Figure 27:
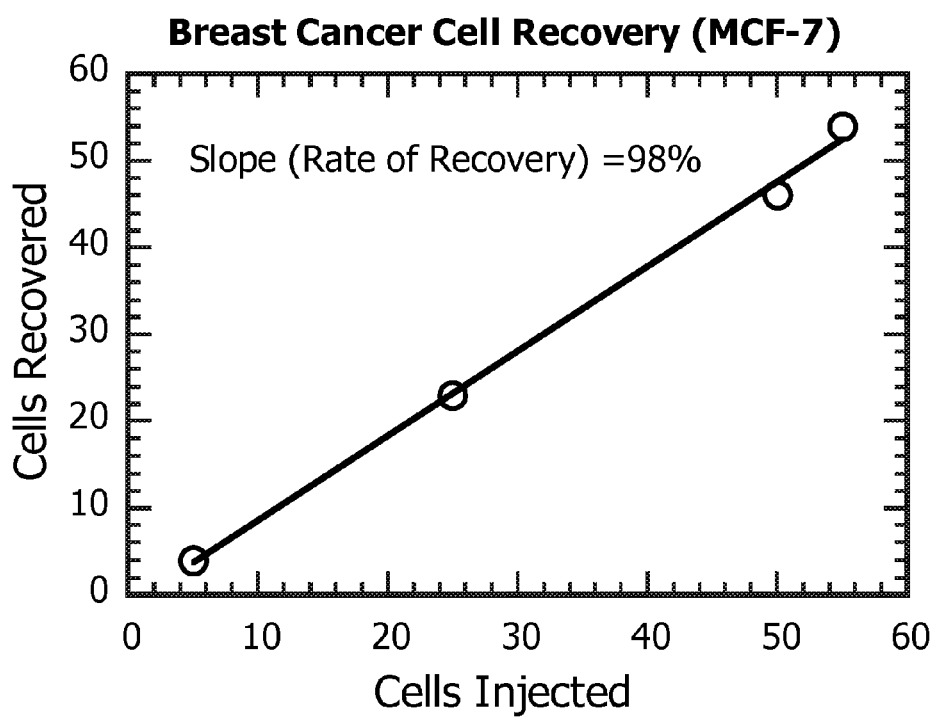
FIG. 27 shows a recovery rate of cancer cells from whole human blood spiked with breast cancer cells.

FIG. 27 shows the number of cancer cells recovered from multiple runs. The curve fit through the recovery data yields a straight line with a slope, which is equivalent to the rate of recovery, of 98%.

Figure 28:
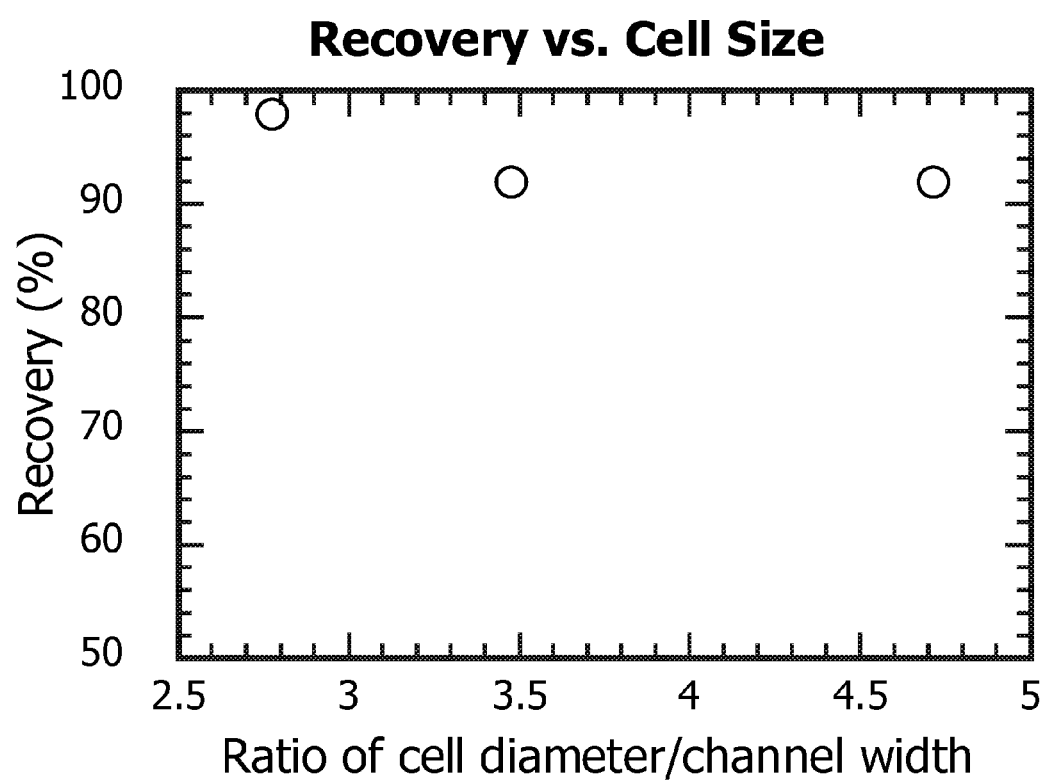
FIG. 28 shows a percentage of cancer cell recovered when the exclusion condition (the relative ratio of cell diameter and the channel width) is altered.

Different lines of cancer cells were tested in the chip. Various channel widths were used to understand the degree of deformability the cancer cells may withstand. Again, whole human blood spiked with cancer cells was used. FIG. 28 shows the cell recovery as a function of the ratio of cell diameter to the channel width, which is an indirect measurement of cell deformation should the cell manage to squeeze through the channel. Because the cells are significantly larger than the channel width (2-5 times) and the channel height is always larger than the cell diameter, thus forming a 1-D channel, the recovery is consistently above 90%, demonstrating low rates of cell loss.

Embodiments of devices in accordance with the present invention may be used for all screening of circulating tumor cells in any cancer, which includes, but is not limited to: oral cancer, nasopharynx cancer, other pharynx cancers, oesophagus cancer, stomach cancer, colon and rectum cancers, liver cancer, pancreatic cancer, larynx cancer, lung cancer, skin cancer, breast cancer, cervical cancer, corpus uteri cancer, ovarian cancer, prostate cancer, testicular cancer, kidney cancer, bladder cancer, brain cancer, thyroid cancer, non-Hodgkin lymphoma, Hodgkin lymphoma, multiple myeloma, and leukaemia.

Blood is the best place to find CTCs from the point of patient comfort and convenience. However, blood is not where CTCs tend to exist in high concentration. For a long time, CTCs were detected mainly by looking in the bone marrow (e.g. spinal aspirate). It is also possible to find exfoliated tumor cells in urine (for prostate cancer), sputum/lung fluid (lung cancer) and other body fluids.

In such cases the task of isolating tumor cells is much simpler; however, because these fluids may not necessarily circulate in the body. However, the cells isolated may not directly indicate the metastatic potential.

Devices in accordance with embodiment of the present invention may be used for screening tumor cells from any body fluid, including but not limited to blood, cerebrospinal fluid, synovial fluid, aqueous humour, vitreous humour, amniotic fluid, bile, cerumen (earwax), Cowper's fluid (pre-ejaculatory fluid), Chyle, Chyme, female ejaculate, interstitial fluid, lymph fluid, menses, breast milk, mucus (including snot and phlegm), pleural fluid, pus, saliva, sebum, semen, serum, sweat, tears, urine, vaginal lubrication, and feces.

Because biofluid samples may contain contaminations such as skin debris, clots, and other undesirable components, embodiments of a device in accordance with the present invention may incorporate additional pre-enrichment protocols, which include, but are not limited to: filters to eliminate gross contamination or clots; reagents to lyse blood cells, reagents to stabilize cell integrity, reagents for selective binding of blood cells or other components in blood to channel surfaces, or to beads in the channel or device, or to other materials that are packed within the channel or device; non-specific absorption of the blood cells or other components in blood to solid surfaces or particles in the channel; chromatographic, dielectrophoretic, magnetic, or other separation methods to remove undesired components in blood.

Embodiments of a device in accordance with the present invention may incorporate assay protocols following the cell isolation or enrichment, which includes, but is not limited to: nucleic-acid based methods such as RNA extraction (with or without amplification), cDNA synthesis (reverse transcription), gene microarrays, DNA extraction, Polymerase Chain Reactions (PCR) (single, nested, quantitative real-time, or linker-adapter), or DNA-methylation analysis; cytometric methods such as fluorescence in situ hybridization (FISH), laser capture microdissection, fluorescence activated cell sorting (FACS), cell culturing, or comparative genomic hybridization (CGH) studies; and chemical assay methods such as electrophoresis, Southern blot analysis or enzyme-linked immunosorbent assay (ELISA).

In one example, the present subject matter includes a substrate material including, but not limited to, polymeric materials (polydimethylsiloxane (PDMS), polymethylmethacrylate (PMMA), polyethylene, polyester (PET), polytetrafluoroethylene (PTFE), polycarbonate, polyvinyl chloride, fluoroethylpropylene, lexan, polystyrene, cyclic olefin copolymers, polyurethane, polyestercarbonate, polypropylene, polybutylene, polyacrylate, polycaprolactone, polyketone, polyphthalamide, cellulose acetate, polyacrylonitrile, polysulfone, epoxy polymers, thermoplastics, fluoropolymer, and polyvinylidene fluoride, polyamide, polyimide), inorganic materials (glass, quartz, silicon, GaAs, silicon nitride), fused silica, ceramic, glass (organic), metals and/or other materials and combinations thereof.

In addition, the substrate can be fabricated of porous membranes, woven or non-woven fibers (such as cloth or mesh) of wool, metal (e.g. stainless steel or Monel), glass, paper, or synthetic (e.g. nylon, polypropylene, and various polyesters), sintered stainless steel and other metals, and porous inorganic materials such as alumna, silica or carbon.

The flow can be delivered by, for example, methods and devices that induce hydrodynamic fluidic pressure, which includes but is not limited to those that operate on the basis of mechanical principles (e.g. external syringe pumps, pneumatic membrane pumps, vibrating membrane pumps, vacuum devices, centrifugal forces, and capillary action); electrical or magnetic principles (e.g. electroosmotic flow, electrokinetic pumps piezoelectric/ultrasonic pumps, ferrofluidic plugs, electrohydrodynamic pumps, and magnetohydrodynamic pumps); thermodynamic principles (e.g. gas bubble generation/phase-change-induced volume expansion); surface-wetting principles (e.g. electrowetting, chemically, thermally, and radioactively induced surface-tension gradient).

In addition, the fluid drive force can be provided by gravity feed, surface tension (like capillary action), electrostatic forces (electroosmotic flow), centrifugal flow (substrate disposed on a compact disc and rotated), magnetic forces (oscillating ions causes flow), magnetohydrodynamic forces and a vacuum or pressure differential.

Fluid flow control devices, such as those enumerated with regard to methods and devices for inducing hydrodynamic fluid pressure or fluid drive force, can be coupled to an input port or an output port of the present subject matter. In one example, multiple ports are provided at either or both of the inlet and outlet and one or more ports are coupled to a fluid flow control device.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

What is claimed is:

1. A method of isolating cancer cells, the method comprising:
   passing a biofluid through a flow channel having a bend configured to impart a flow in a direction towards an aperture, wherein the flow channel is enclosed within walls of a microfluidic device and comprises the aperture configured to impede movement of a cancer cell while allowing flow of the biofluid through the aperture, wherein movement of the cancer cell is impeded by a cross-sectional shape of the aperture, wherein the cancer cell covers about 75% or less of a cross-sectional area of the aperture, whereby the cross-sectional area of the aperture reduces the fluid pressure applied to the cell.

2. The method of claim 1 further comprising diluting the biofluid prior to passage through the flow channel.

3. The method of claim 1 further comprising stabilizing the biofluid with a fixative prior to passage through the flow channel.

4. The method of claim 1 further comprising treating the biofluid with a material that binds preferentially to the cancer cell to assist in visualization of the cancer cells.

5. The method of claim 4 wherein the biofluid is treated with the material having fluorescent, magnetic, electroactive, bioactive, or photoactive properties.

6. The method of claim 1 further comprising visualizing the cancer cell with a microscope through a transparent wall of the channel.

7. The method of claim 1 further comprising:
   collecting the cancer cell; and
   treating the collected cancer cell with a material having fluorescent, magnetic, electroactive, bioactive, or photoactive properties.

8. The method of claim 7 wherein the material is configured to identify a subpopulation of cancer cells.

9. The method of claim 8 subpopulation of cancer cells comprises a putative cancer stem cell.

10. A method comprising:
    collecting one or more cancer cells by flowing a sample of a biofluid through a first flow channel having a bend configured to impart a flow in a direction towards an aperture, wherein the first flow channel is enclosed in a microfluidic device and further comprises the aperture defined by a smallest dimension of a second flow channel, the smallest dimension smaller than a dimension of the one or more cancer cells, wherein the cross-sectional area of the aperture is configured to reduce the fluid pressure applied to the cancer cells, while allowing the cancer cell to cover about 75% or less of the cross-sectional area while fluid flows around the one or more cancer cells into the second flow channel; and
    exposing the cancer cells to a material configured to bind preferentially thereto; and
    counting a number of the collected cancer cells in order to evaluate a likelihood of metastasis.

11. The method of claim 10 wherein the cancer cells are exposed to the material prior to collection.

12. The method of claim 10 wherein the cancer cells are exposed to the material after the collection.

13. The method of claim 10 further comprising determining cancer diagnosis or prognosis based upon the number of cancer cells collected.

14. The method of claim 10 further comprising determining an effectiveness of cancer treatment based upon the number of cancer cells collected.

* * * * *